US012343290B2

(12) United States Patent
Pole et al.

(10) Patent No.: US 12,343,290 B2
(45) Date of Patent: Jul. 1, 2025

(54) OPHTHALMIC INCISIONAL PROCEDURE INSTRUMENT AND METHOD

(71) Applicant: EYEMDENGINEERING LLC, Leawood, KS (US)

(72) Inventors: Christopher J Pole, Overland Park, KS (US); David D Scott, St. Louis Park, MN (US)

( * ) Notice: Subject to any disclaimer, the term of this patent is extended or adjusted under 35 U.S.C. 154(b) by 384 days.

(21) Appl. No.: 18/102,179

(22) Filed: Jan. 27, 2023

(65) Prior Publication Data
US 2023/0165720 A1    Jun. 1, 2023

Related U.S. Application Data

(63) Continuation-in-part of application No. 17/028,660, filed on Sep. 22, 2020, now abandoned, which is a continuation-in-part of application No. 15/899,784, filed on Feb. 20, 2018, now Pat. No. 10,779,990.

(60) Provisional application No. 62/460,660, filed on Feb. 17, 2017.

(51) Int. Cl.
*A61F 9/01*  (2006.01)
*A61F 9/013*  (2006.01)

(52) U.S. Cl.
CPC .................. *A61F 9/0133* (2013.01)

(58) Field of Classification Search
CPC ......... A61B 17/32053; A61B 2017/306; A61F 9/0133; A61F 9/0136
See application file for complete search history.

(56) References Cited

U.S. PATENT DOCUMENTS

| | | | |
|---|---|---|---|
| 624,595 | A | 5/1899 | Williams |
| 770,019 | A | 9/1904 | Neireiter |
| 902,104 | A | 10/1908 | Neireiter |
| 4,619,259 | A | 10/1986 | Graybill et al. |
| 4,691,716 | A | 9/1987 | Tanne et al. |
| 4,739,761 | A | 4/1988 | Grandon et al. |
| 4,796,623 | A | 1/1989 | Krasner et al. |
| 5,316,410 | A | 5/1994 | Blume |
| 5,368,604 | A | 11/1994 | Kilmer et al. |
| 5,403,335 | A | 4/1995 | Loomas et al. |

(Continued)

OTHER PUBLICATIONS

"International Search Report and Written Opinion for Application No. PCT/US2014/020848, Mailed Nov. 11, 2014".

*Primary Examiner* — Alexander J Orkin
(74) *Attorney, Agent, or Firm* — Mark E. Brown

(57) ABSTRACT

An incisional instrument and method of use for creating accurate, reproducible surgical incisions. An exemplary embodiment includes an incisional instrument configured for attachment to a patient's eye and for use performing arcuate limbal relaxing incisions (LRIs). The incisional instrument is made up of two coaxial, interconnecting pieces: a docking piece and a cutting piece. The docking piece includes a suction mechanism and is configured for being secured to a patient's eye just outside the corneal limbus. The cutting piece is configured to fit flush within the docking piece and includes cutting blades and one or more handles for rotating the cutting piece relative to the docking piece. When assembled, the cutting blades extend into a patient's eye a desired LRI depth. An embodiment further includes an arcuate guide template with stoppers for providing lateral, arcuate stops for precise cuts in the desired LRI locations. An LRI method includes the steps of utilizing the incisional instrument in an ophthalmologic LRI procedure.

17 Claims, 23 Drawing Sheets

(56) References Cited

U.S. PATENT DOCUMENTS

| | | |
|---|---|---|
| 5,938,674 A | 8/1999 | Terry |
| 6,019,472 A | 2/2000 | Koster et al. |
| 6,143,010 A | 11/2000 | Silvestrini et al. |
| 6,251,118 B1 | 6/2001 | Proudfoot et al. |
| 6,613,061 B1 | 9/2003 | Olson et al. |
| 7,166,117 B2 | 1/2007 | Hellenkamp |
| 9,795,509 B2 | 10/2017 | Heitel et al. |
| 10,779,990 B2 | 9/2020 | Pole et al. |
| 2002/0103481 A1 | 9/2002 | Fader et al. |
| 2005/0100412 A1 | 5/2005 | Houck |
| 2006/0088382 A1 | 4/2006 | Nelson |
| 2006/0287663 A1 | 12/2006 | Gayheart et al. |
| 2007/0093795 A1 | 4/2007 | Melcher et al. |
| 2008/0033463 A1 | 2/2008 | Stoken |
| 2009/0137989 A1 | 5/2009 | Kataoka |
| 2009/0182310 A1 | 7/2009 | Gertner et al. |
| 2009/0182312 A1 | 7/2009 | Gertner et al. |
| 2010/0022994 A1 | 1/2010 | Frey et al. |
| 2011/0064521 A1 | 3/2011 | Schafer |
| 2011/0319873 A1 | 12/2011 | Raksi et al. |
| 2012/0283557 A1 | 11/2012 | Berlin |
| 2013/0041354 A1 | 2/2013 | Brownell et al. |
| 2013/0103014 A1 | 4/2013 | Gooding et al. |
| 2018/0036168 A1 | 2/2018 | Heitel et al. |

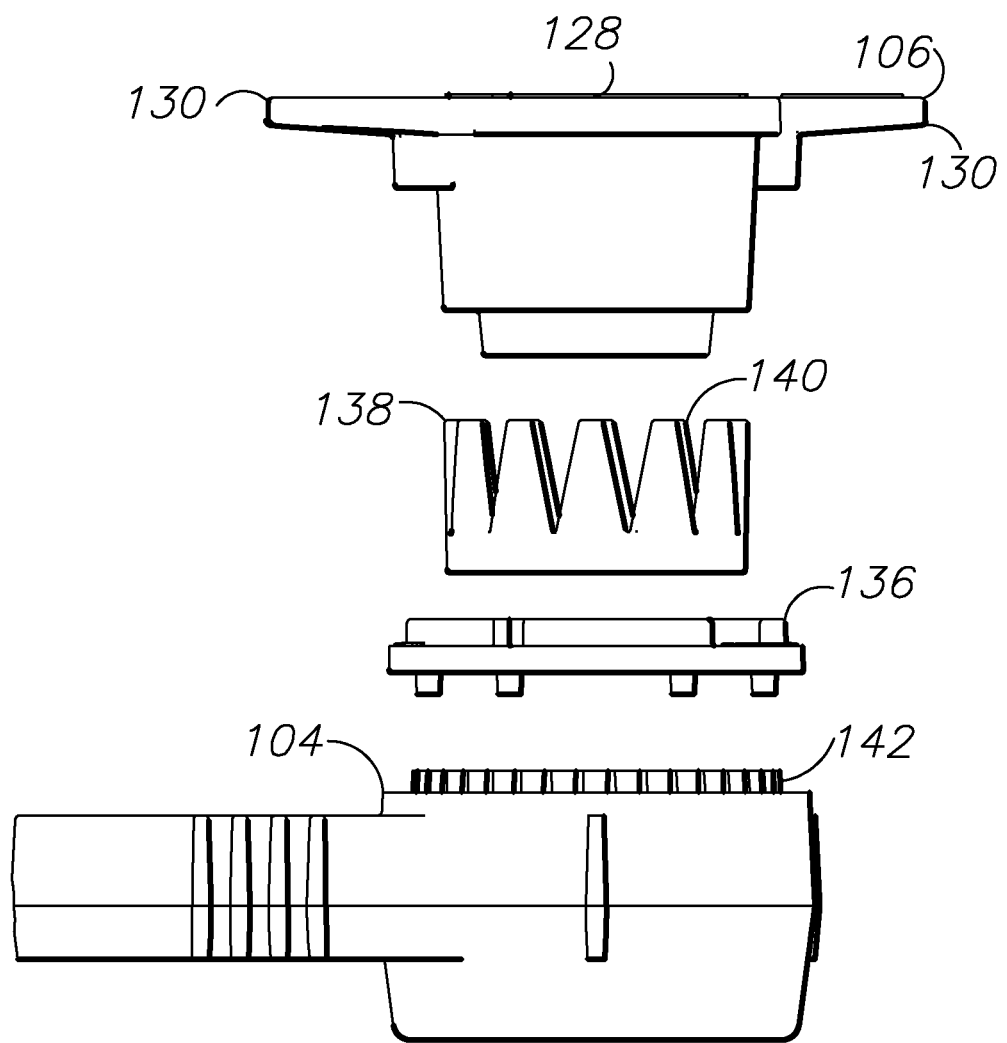
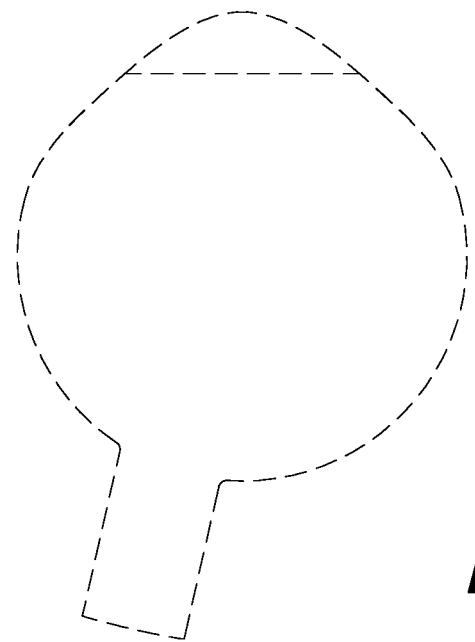
FIG. 20

OPHTHALMIC INCISIONAL PROCEDURE INSTRUMENT AND METHOD

CROSS-REFERENCE TO RELATED APPLICATION

This application is a continuation-in-part of and claims priority in U.S. patent application Ser. No. 17/028,660, filed Sep. 22, 2020, which is a continuation of and claims priority in U.S. patent application Ser. No. 15/899,784, filed Feb. 20, 2018, now U.S. Pat. No. 10,779,990, which claims priority in U.S. Provisional Patent Application No. 62/460,660, filed Feb. 17, 2017, all of which are incorporated herein by reference.

BACKGROUND OF THE INVENTION

1. Field of the Invention

The present invention relates generally to an incisional instrument and method for performing surgical incisions, and more specifically to an ophthalmic incisional instrument for surgical correction of astigmatism and a corresponding method of performing a surgical procedure.

2. Description of the Related Art

Astigmatism is a type of visual refractive error caused by aberrant meridians of curvature around an otherwise spherical cornea or lens. These mismatched curvatures cause images to not be properly focused on the retina, resulting in blurry or distorted vision. Other symptoms of astigmatism may include eyestrain, discomfort, headaches, difficulty with night vision, and squinting. Astigmatism is very common, with studies showing approximately 15-30% of the adult population having astigmatism greater than one diopter.

Incisional methods for correction of corneal astigmatism have been popular since the 1980s. Originally, incisions to correct corneal astigmatism were made in the para-central cornea, but over the years, ophthalmologists have gradually placed these incisions further from the center of the eye because of problems with healing, predictability, and glare. Today, incisions to correct corneal astigmatism are placed in the surgical limbus, which is located at the intersection of the cornea and the sclera. These incisions are commonly referred to as limbal relaxing incisions (LRIs). Based on the degree and distribution of corneal astigmatism to be corrected, surgeons plan the arc and depth of the incisions in order to make the cornea more spherical and to improve the patient's vision.

A cataract is another very common optical condition in which the natural lens of the eye becomes cloudy, causing distorted vision. Cataract surgery—in which a patient's natural lens having a cataract is removed and replaced with an artificial intraocular lens (IOL) to restore clear vision—is currently one of the most common surgical procedures in the United States. Most people develop cataracts as they age, and thus, many patients undergo cataract surgery in each eye to correct their vision. With the prevalence of cataract treatment procedures, many ophthalmologists recommend that patients undergo surgical correction of astigmatism at the same time as cataract surgery. This option is very popular among patients because, when coupled with the spherical correction from a new intraocular lens, surgical astigmatism correction can often give these patients an opportunity to be completely free of eyeglasses and contact lenses.

Currently, there are two common methods for performing LRIs: manual incision and use of a femtosecond laser. Manual incision procedures are commonly performed with surgeons using marking pens to indicate the areas of paired incisions and then using blades, typically made of diamond or sometimes metal, to cut the LRIs. However, this method of manual incision is generally reliant on the surgeon to perform LRIs at the correct depth, length, and curvature.

A femtosecond laser accommodates automation of many factors of LRIs. This method utilizes a suction cup to hold the patient's eye in place while a laser creates the incisions from above by generating a light beam and using a scanner to deflect the light beam to deliver a treatment pattern to the surgical limbus. Femtosecond lasers are versatile, as they can be used to further automate other steps required in cataract surgery. However, the costs associated with using femtosecond lasers tend to be relatively high. Additionally, some current literature suggests that the use of such lasers does not improve outcomes in cataract surgery.

Thus, there is a strong need for a simple, inexpensive instrument and method of use thereof to assist ophthalmologists in creating accurate and reproducible manual limbal relaxing incisions (LRIs). Such an instrument could make LRIs during cataract surgery much more prevalent and provide a number of benefits for patients. Such benefits to patients include the cosmetic benefits of no longer needing to wear glasses and the benefits of no longer needing to deal with the hassle and the risks of corneal ulcers or abrasions from contact lenses. Additionally, it could ease the financial burden of having to continually purchase glasses and contact lenses. Further, such an instrument could help many patients in lower resource areas of the world, who do not have the means to obtain adequate glasses regularly, with better access to improved vision.

Currently, there are ophthalmic incisional instruments on the market consisting of a spring-loaded rod having a cutting blade in which the exposed length of the blade can be controlled with a micrometer thread. However, with such an instrument, the surgeon is still responsible for accurately guiding the instrument along the limbus and making the incision to the desired length.

Another instrument, called the Universal Limbal Relaxing Incision Guide, disclosed in U.S. Pat. No. 8,231,643, includes two concentric rings for guiding a surgeon's blade to make an incision of the appropriate measured length. This instrument helps reduce some issues with incision length and blade position of LRIs. However, the Universal Limbal Relaxing Incision Guide does not attach or anchor to the eye during the surgical procedure, making the accuracy of the LRIs reliant on the surgeon or an assistant holding the instrument in the proper position without moving. Also, there is no cutting blade portion of the Universal Limbal Relaxing Incision Guide, meaning a separate blade must be used along with it to cut the LRIs.

Heretofore there has not been available a system or method for performing LRIs with the advantages and features of the present invention.

SUMMARY OF THE INVENTION

The present invention provides an ophthalmic incisional instrument and method for creating accurate and reproducible surgical incisions. In the practice of an aspect of the present invention, the ophthalmic incisional instrument is configured for attachment to a patient's eye and for use cutting circumferential limbal relaxing incisions (LRIs) of a desired depth, length, and curvature. In an exemplary embodiment, the incisional instrument includes two concentric, interlocking pieces: a docking piece and a cutting piece.

The docking piece includes a suction mechanism and is configured for being secured to a patient's eye just outside the corneal limbus. The cutting piece is configured to fit flush inside the docking piece and includes two cutting blades and one or more handles configured to rotate the cutting piece relative to the docking piece. When assembled, the cutting blades of the cutting piece extend beyond the inner portion of the bottom of the docking piece a length equal to the desired depth of LRIs to be cut. Further, the cutting piece is sized and the cutting blades are positioned such that the cutting piece is configured for making incisions along the corneal limbus when the instrument is assembled. The docking piece may also include measurement markings around its circumference, and the cutting piece may include markings configured for matching up with the docking piece markings for proper positioning and measuring of incisions.

In the practice of an aspect of the present invention, a patient's eye is first marked for desired LRIs to be cut. Next, the docking piece is docked to the eye in desired position via suction. The surgeon then matches the markings on the cutting piece with the appropriate measurement markings on the docking piece to line up the cutting blades for making incisions at the desired positions. Once the markings are properly aligned, the cutting piece is inserted completely into the docking piece so that the cutting piece is flush against the docking piece, resulting in the cutting blades being inserted a predetermined, desired depth into the patient's eye. The surgeon then rotates the cutting piece relative to the docking piece a predetermined direction and length via the one or more handles, using the measurement markings on the docking piece for reference, to produce a pair of LRIs, each having an accurate depth, length, and arcuate path.

In another embodiment of the present invention, the incisional instrument further includes an arcuate guide template configured for attachment to the docking piece and having raised stoppers for providing lateral, arcuate, mechanical stops for the cutting piece. Such arcuate guide template raised stoppers are configured for making contact with guides on the cutting piece to prevent over rotation of the cutting piece outside the designated area for an LRI procedure.

In other aspects of the present invention, the docking pieces include handles and grips for a user to easily grasp and hold the docking pieces in position. The docking pieces can also include internal housings for vacuum tubing.

The present invention accommodates creating efficient, accurate, and reproducible LRIs without requiring use of a laser.

BRIEF DESCRIPTION OF THE DRAWINGS

The drawings constitute a part of this specification and include exemplary embodiments of the present invention illustrating various objects and features thereof.

FIG. 20 is an exploded, side elevational view.

DETAILED DESCRIPTION OF THE PREFERRED EMBODIMENTS

I. Introduction and Environment

Figure 1:
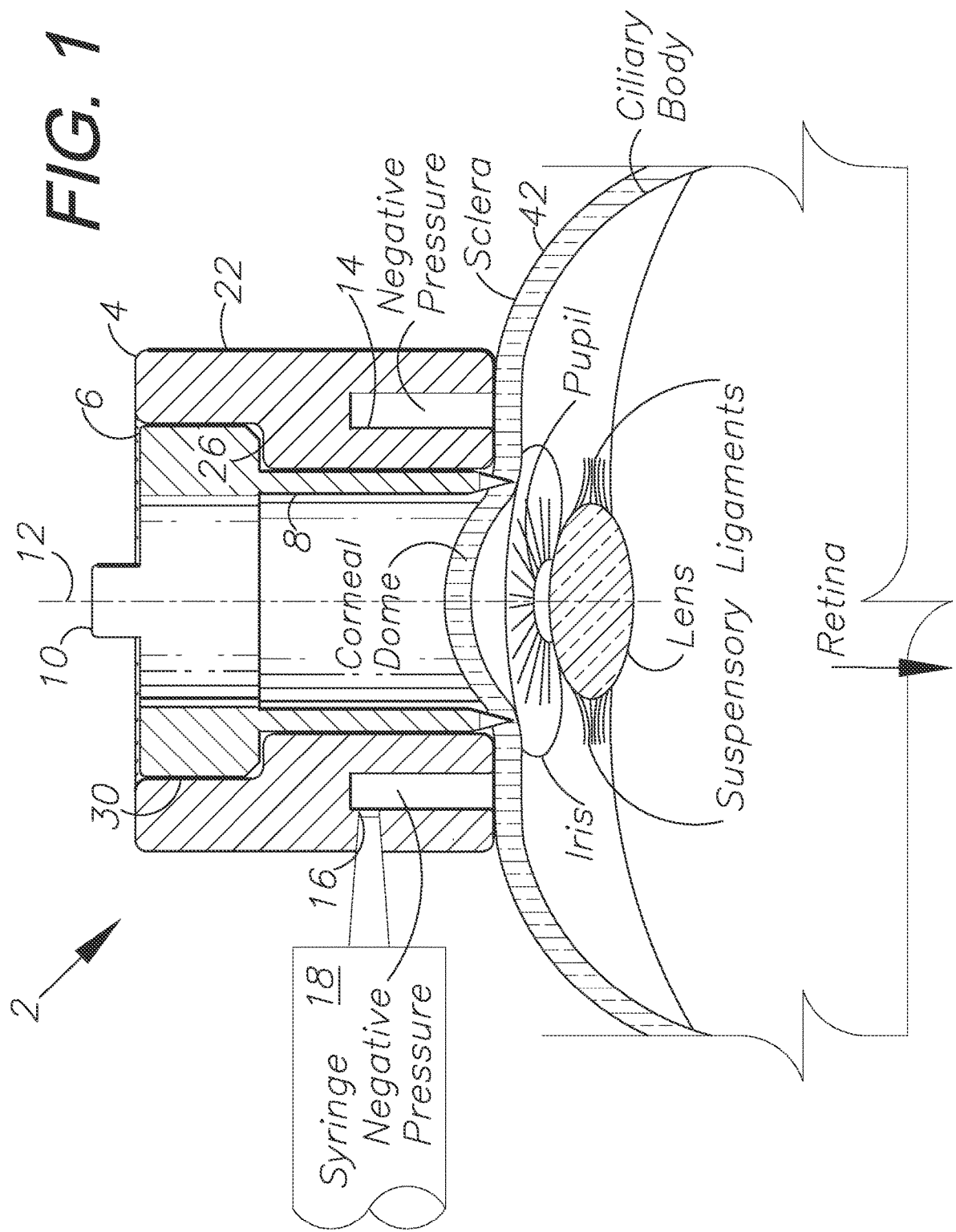
FIG. 1 is a vertical, cross-sectional view of an ophthalmic incisional (e.g., LRI) instrument comprising an embodiment or aspect of the present invention, shown placed on an LRI treatment patient's eye.

As required, detailed aspects of the present invention are disclosed herein, however, it is to be understood that the disclosed aspects are merely exemplary of the invention, which may be embodied in various forms. Therefore, specific structural and functional details disclosed herein are not to be interpreted as limiting, but merely as a basis for the claims and as a representative basis for teaching one skilled in the art how to variously employ the present invention in virtually any appropriately detailed structure.

Certain terminology will be used in the following description for convenience in reference only and will not be limiting. For example, up, down, front, back, right, and left refer to the invention as orientated in the view being referred to. The words "inwardly" and "outwardly" refer to directions toward and away from, respectively, the geometric center of the aspect being described and designated parts thereof. Additionally, anatomical terms are given their usual meanings. For example, proximal means closer to the trunk of the body, and distal means further from the trunk of the body. Said terminology will include the words specifically mentioned, derivatives thereof, and words of similar meaning.

II. Ophthalmic Incisional Instrument 2

In a preferred embodiment of the present invention, shown in FIGS. 1-8, an incisional instrument 2 is configured for use in cutting accurate and reproducible limbal relaxing incisions (LRIs) for correcting corneal astigmatism. However, alternative embodiments of the present invention can be used for making any other type of arcuate, surgical incisions or any other non-surgical, arcuate cuts. In a preferred embodiment, the incisional instrument 2 includes two coaxial pieces: a docking piece 4 and a cutting piece 6. The pieces 4, 6 are generally coaxial about a rotational axis 12. The cutting piece 6 is configured for being inserted into the docking piece 4 and is rotatable therein.

In this embodiment, each piece is generally cylindrical in shape, with an open center. The docking piece 4 is configured for being secured to a patient's eye with suction. The cutting piece 6, in this embodiment, is configured for mounting a pair of cutting blades 8 and for fitting coaxially within the docking piece 4 when the instrument 2 is assembled. The cutting piece 6 cutting blades 8 are each of a precise length so that when the cutting piece 6 is flush up against and within the docking piece 4, each cutting blade 8 extends beyond the bottom, or proximal side, of the docking piece 4 a length equal to a desired depth of incisions to be cut. The cutting piece 6 also includes one or more handles 10 for rotating the cutting piece 6 relative to the docking piece 4 to make arcuate incisions.

The docking piece 4 has a cylindrical surface 22 and includes a suction chamber 14 open to the proximal side, or bottom, for accommodating firm, releasable attachment to the sclera, just outside the corneal limbus, of a patient's eye 42 by suction. The docking piece 4 is made of a rigid material which holds its shape under force or pressure. In a preferred embodiment, the docking piece 4 is made of hard plastic, but other embodiments may be made of other rigid materials such as, but not limited to, metal or ceramic. The outer edge surface of the docking piece 4, in this embodiment, includes a side opening 16 to the suction chamber 14 through which sub-atmospheric or negative pressure, or suction, can be applied to the suction chamber 14. In a preferred embodiment, the side opening 16 is sized to fit and seal around tubing connected to a syringe 18 for applying sub-atmospheric pressure, or negative pressure, to the suction chamber 14, as shown in FIG. 1. However, alternative embodiments may include tubing connected to a vacuum or sub-atmospheric pressure source configured for applying sub-atmospheric pressure to the suction chamber 14 through the side opening 16 or any other mechanism for applying sub-atmospheric pressure to the suction chamber 14 through the opening 16.

The docking piece 4 further includes an open center 24 configured for the cutting piece 6 to fit inside and for a surgeon to see through the docking piece 4 below to a patient's eye 42. The docking piece open center 24 forms a receiver for the cutting piece 6. The docking open center 24 includes a larger center opening at its distal end and a step portion 26 for providing a mechanical stop for the cutting piece 6 when the cutting piece is inserted into the docking piece 4. The larger opening above the step portion 26 is sized to fit flush around the cylindrical outer surface 30 of the cutting piece 6, with the step 26 contacting the proximal side, or underside, of the cylindrical surface 30 of the cutting piece 6 when the incisional instrument 2 is fully assembled. The portion of the central opening 24 of the docking piece 4 proximally from, or beneath, the step portion 26 is sized to fit flush around the cutting blades 8 of the cutting piece 6.

The cutting piece 6, in the exemplary embodiment shown in FIGS. 1-8, includes a cylindrical outer surface 30 mounting two cutting blades 8 and having an open center 32. The cutting blades 8 are configured for being equal in length and are positioned in 180-degree opposed relation, mounted from the proximal end of the cylindrical outer surface 30 of the cutting piece 6. In this arrangement, the cutting blades 8 are configured for making two symmetrical cuts of equal length, depth, and curvature. In alternative embodiments, the cutting piece 6 may only mount one cutting blade 8 configured for making one arcuate cut at a time. In further alternative embodiments, the cutting piece 6 may include more than two cutting blades 8 spaced apart as necessary for desired cutting configurations. The cutting piece 6 also includes one or more handles 10 for rotating the cutting piece 6 relative to the docking piece 4. In the embodiment shown in FIGS. 1-8, the cutting piece 6 includes two handles 10, which provide torque for effective rotation of the cutting piece 6 in either direction. Alternative embodiments may include only one handle 10 or any number of handles 10, as desired, for rotating the cutting piece 6 relative to the docking piece 4. Further embodiments may include a cutting piece 6 without a center opening 32.

The mechanical stop for the cutting piece 6 in assembled position within the docking piece 4 provided by the step portion 26 of the docking piece 4 is configured for keeping the cutting blades 8 exposed beyond the proximal end, or bottom, of the docking piece 4 a length equal to the desired incision depth. In an exemplary embodiment, the cutting blades 8 are made up of metal capable of making accurate surgical incisions. In alternative exemplary embodiments, the cutting blades 8 may be diamond-shaped for making surgical incisions or any other configurations of suitable materials capable of making accurate incisions. Different lengths of cutting blades 8 may be used as desired for making incisions having different desired depths.

In an exemplary embodiment, the cutting blades 8 are detachable from the cutting piece 6 and replaceable with cutting blades 8 of another length. In such embodiments, the cutting blades 8 may connect into an inner surface of the cutting piece cylindrical surface 30. In other embodiments, cutting blades 8 are permanently affixed to the cutting piece 6. In such embodiments, different cutting pieces 6 having different sizes of cutting blades 8 would be available to surgeons depending on the desired depth of incisions to be made. Similarly, in preferred embodiments, different sizes of docking pieces 4 having varying diameters and corresponding cutting pieces 6 with corresponding varying diameters are available to surgeons depending on the dimensions of the patient's eye to be treated. In various embodiments, the cutting blades 8 may be disposable or configured for reuse after proper sterilization. Additionally, in some embodiments, the entire incisional instrument 2 may be disposable or configured for reuse after proper sterilization. Other embodiments may include a reusable docking piece 4 with a disposable cutting piece 6 or any other combination of disposable and reusable individual pieces.

The incisional instrument 2 of the present invention further includes measurement markings 36 and one or more reference markings 38 for measuring the arcuate incisions made with the instrument 2. In a preferred embodiment, the docking piece 4 includes measurement markings 36 on the distal side, or top, of the docking piece cylindrical surface 22. In the exemplary embodiment shown in FIGS. 1-8, the measurement markings 36 represent degrees, from 0 to 360 degrees, with representative rotational indicia 34 providing references for the surgeon. However, in alternative embodiments, the measurement markings 36 may represent radians, gradians, revolutions, or any other units of measurement of an angle. Optionally, the docking piece 4 may further include one or more rotational indicia measurement markings 28 on the outer edge of the docking piece cylindrical surface 22 for the surgeon to reference, as shown by the "0" marking on the outer edge of the docking piece cylindrical surface 22 in FIGS. 2 and 3.

The incisional instrument 2 further includes one or more reference markings 38 on the cutting piece 6 for aligning the cutting piece 6 with the measurement markings 36 on the docking piece 4. The measurement markings 36 and reference markings 38 allow the user to effectively make cuts with the cutting blades 8 in the correct, desired incision locations. Preferably, the cutting piece reference markings 38 are located on the distal side, or top, of the cutting piece cylindrical surface 30 directly above, or distally from, the cutting blades 8. However, in alternative embodiments, the cutting piece reference markings 38 may be offset from the cutting blades 8, for instance, 90 degrees from the cutting blades 8. In the preferred embodiment shown in FIGS. 1-8, the handles 10 of the cutting piece 6 are offset from the cutting blades 8 and reference markings 38 by 90 degrees, accommodating easy alignment of the reference markings with the measurement markings 36 on the docking piece 4. Alternatively, the handles 10 may be directly above, or distal from, the cutting blades 8 or in any other handle configuration.

Prior to using the incisional instrument 2 of the present invention to perform symmetrical and precise limbal relaxing incisions (LRIs), a surgeon would first mark the patient's eye 42 with a marking pen at the desired locations for the starting point of incisions in the surgical limbus. Next, the docking piece 4 of the incisional instrument 2 is placed on the patient's eye 42 just outside and adjacent to the surgical limbus and the desired incision locations. With the docking piece 4 in proper position on the eye 42, sub-atmospheric pressure is applied to the suction chamber 14 of the docking piece 4 through the side opening 16 via a syringe 18 or some other sub-atmospheric or negative pressure mechanism. Sub-atmospheric pressure applied to the suction chamber 14 attaches the docking piece 4 to the eye 42 and docks the docking piece 4 in the proper position. Next, using the measurement markings 36 and reference markings 38, the cutting piece 6, with cutting blades 8 of a desired length to achieve incisions of the desired depth, is properly aligned with the docking piece 4 so that the cutting blades 8 are aligned with the desired incision starting points. Once properly aligned, the cutting piece 6 is inserted into the docking piece center opening 24, with the step portion 26 providing a mechanical stop for the cutting piece 6 and resulting in the cutting blades 8 cutting into the patient's eye 42 a desired incisional depth. Once assembled, with the cutting blades 8 cutting into the patient's eye 42, the cutting piece 6 is rotated with the handles 10 relative to the docking piece 4 and the eye 42 for a desired incisional length, using the measurement markings 36 and reference markings 38 to measure the incisions. This process guides the cutting blades 8, resulting in two symmetrical, arcuate incisions of equal depth, length, and curvature. Most commonly, a surgeon would hold the docking piece 4 with his or her non-dominant hand while rotating the cutting piece 6 with his or her dominant hand when performing the LRIs. Once the incisions have been made, the cutting piece 6 is removed from the docking piece 4, sub-atmospheric pressure is removed from the docking piece suction chamber 14 to release the docking piece 4 from the patient's eye 42, and the docking piece 4 is removed from the patient's eye 42.

FIG. 1 shows a cross-sectional, environmental view of an embodiment of the incisional instrument 2 of the present invention with the cutting blades 8 making incisions into the surgical limbus of a patient's eye 42. For reference, FIG. 1 includes some anatomical features of the human eye, including the corneal dome, or cornea; sclera; iris; pupil; lens; suspensory ligament; ciliary body; and a reference to the location of the retina. The surgical limbus, also known as the corneal limbus or simply the limbus, is located at the intersection of the cornea and the sclera and is the desired location for making limbal relaxing incisions (LRIs). In this embodiment, sub-atmospheric pressure is applied to the suction chamber 14 via a syringe 18 through the side opening 16 to the suction chamber 14. Sub-atmospheric pressure in the suction chamber 14 provides attachment of the docking piece 4 to the sclera of the patient's eye 42, docking the docking piece 4 just outside of and adjacent to the corneal limbus. The cutting piece 6 fits flush within the open center 24 of the docking piece cylindrical surface 22. The step portion 26 of the docking piece 4 provides a mechanical stop to the cylindrical surface 30 of the cutting piece 6. With the proximal side of the cutting piece cylindrical surface 30 flush against the step portion 26 of the docking piece 4, the cutting blades 8, mounted from the cutting piece cylindrical surface 30, are flush against the sides of the narrower portion of the docking piece open center 24 proximally from the step portion 26. The cutting blades 8 further extend proximally beyond the proximal end of the docking piece 4 and into the patient's eye 42 at the surgical limbus a desired length, forming incisions of a desired depth. FIG. 1 further shows a handle 10 of the cutting piece 6, which the surgeon can use to rotate the cutting piece 6 relative to the docking piece 4 and the patient's eye 42 as necessary to make the desired LRIs.

Figure 2:
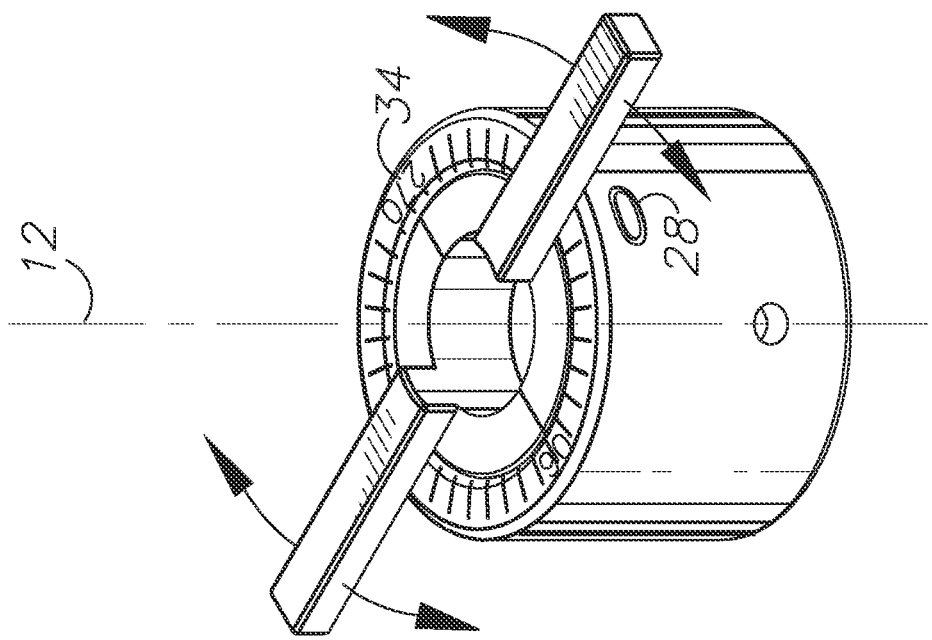
FIG. 2 is an upper, perspective, exploded view of the incisional instrument.

FIG. 2 shows an exploded view of the incisional instrument 2, with the cutting piece 6 separate from and above the docking piece 4. FIG. 2 illustrates the docking piece 4 having an open center 24 and the cutting piece 6 also having an open center 32. The cylindrical surface 30 of the cutting piece 6 is sized to fit within the docking piece open center 24. Further, FIG. 2 particularly illustrates the measurement markings 36 and representative rotational indicia 34 on the distal side of the docking piece 4 and the reference markings 38 on the distal side of the cutting piece 6 for alignment with the measurement markings 36 of the docking piece 4. This embodiment also includes rotational indicia 28 on the side of the docking piece cylindrical surface 22 for reference for the surgeon. In this embodiment, the measurement markings 36 represent degrees. However, as mentioned above, alternative units of angular measurement can be used instead. FIG. 2 shows a preferred embodiment having the reference markings 38 placed above the cutting blades 8 on the distal side of the cutting piece 6 for identification of the location of the cutting blades 8. In this embodiment, the handles 10 are offset 90 degrees from the cutting blades 8 and the reference markings 38 for easy alignment with the measurement markings 36 of the docking piece 4. FIG. 2 also shows the side opening 16 through the outer surface of the docking piece cylindrical surface 22 to the suction chamber 14.

Figure 3:
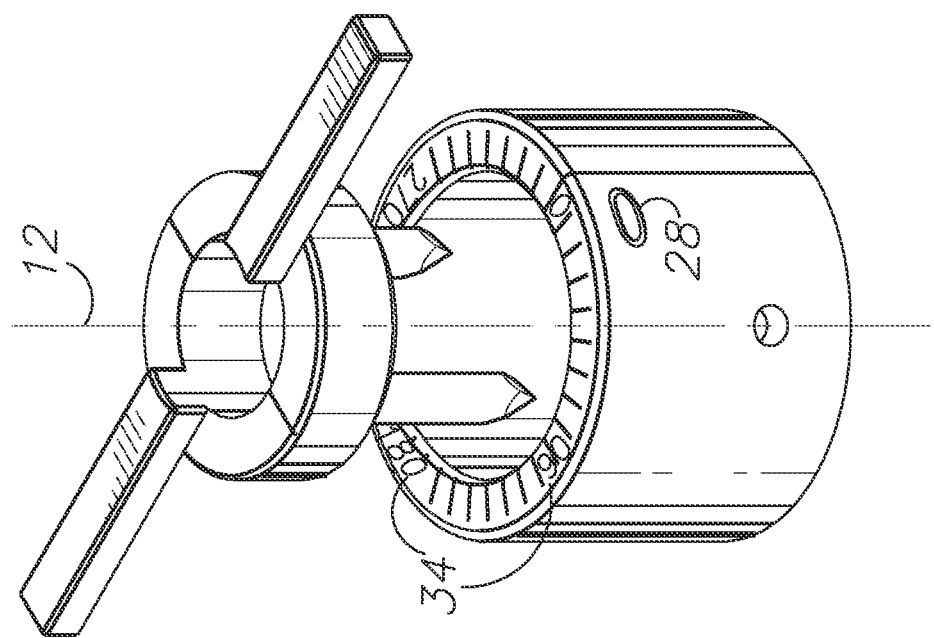
FIG. 3 is an upper, perspective, assembled view of the incisional instrument.

FIG. 3 is an assembled view of the incisional instrument 2 of the present invention, with the cutting piece 6 fully inserted into the center of the docking piece 4, the pieces 4, 6 sharing a rotational axis 12. The cutting piece open center 32 allows a surgeon using the incisional instrument 2 to see through to an underlying patient's eye 42 below with the incisional instrument 2 in assembled position. FIG. 3 shows the alignment of the reference markings 38 with the measurement markings 36 in assembled position for properly positioning and measuring incisions being made with the incisional instrument 2. Directional arrows 46 illustrate that the handles 10 can be used to rotate the cutting piece 6 in either rotational direction relative to the docking piece 4, as desired.

Figure 5:
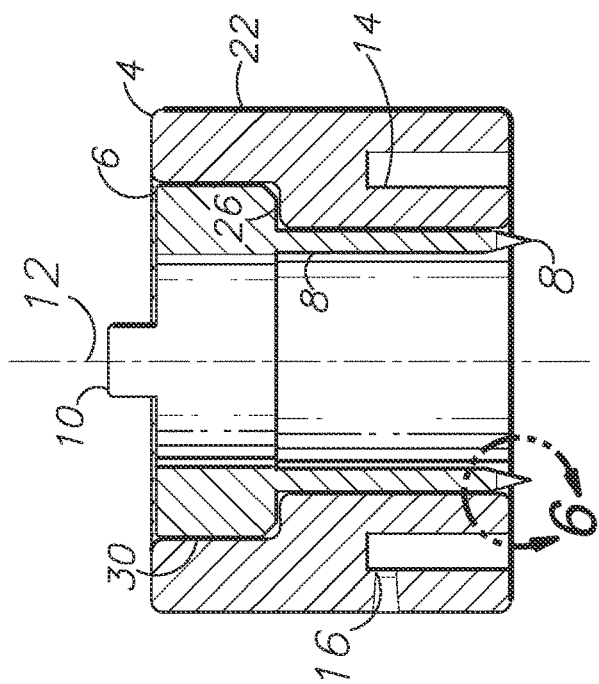
FIG. 5 is a vertical, cross-sectional view of the incisional instrument.
Figure 4:
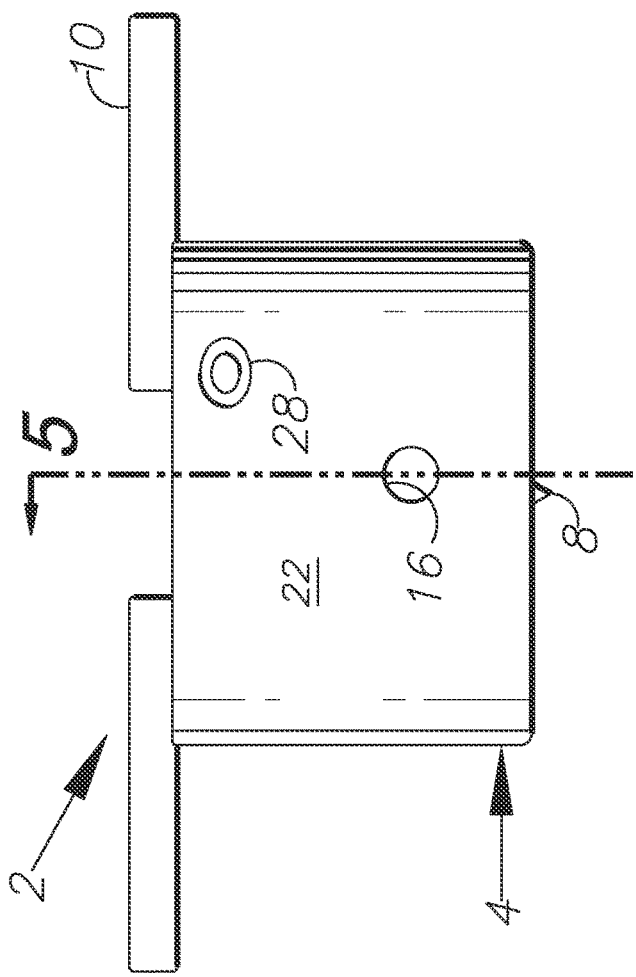
FIG. 4 is a side, elevational view of the assembled incisional instrument.
Figure 6:
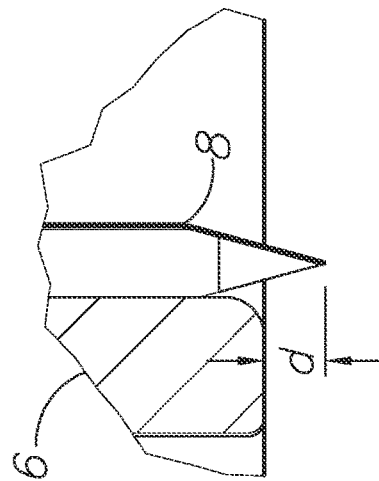
FIG. 6 is an enlarged, fragmentary, cross-sectional view of the incisional instrument showing a cutting blade extending beyond the proximal end of the docking piece in an assembled configuration, taken generally within circle 6 in FIG. 5.

FIG. 4 is a side, elevational view of the incisional instrument 2. Primarily, FIG. 4 displays a cutting blade 8 extending beyond the proximal end of the cylindrical surface 22 of the docking piece 4. FIG. 5 shows a vertical, cross-sectional view of the incisional instrument 2. This cross-section, as shown generally by line 5 in FIG. 4, cuts through the side opening 16 from the outer edge of the docking piece cylindrical surface 22 to the suction chamber 14. The cross-section in FIG. 5 shows the step portion 26 of the docking piece 4 providing a stop for the cylindrical surface 30 of the cutting piece 6 in assembled position. In assembled position, the cutting blades 8, which are mounted from the cutting piece cylindrical surface 30 in an arrangement narrower than the portion of the docking piece center opening 24 proximal from the step portion 26, extend proximally from the cutting piece cylindrical surface 30 and beyond the proximal end of the docking piece 4. FIG. 6 shows an enlarged, fragmentary, vertical, cross-sectional view, taken generally from within circle 6 in FIG. 5, of a cutting blade 8 of the incisional instrument 2 extending proximally past the proximal end of the docking piece 4 by a dimension d. Dimension d is equal to the desired depth of incision.

Figure 8:
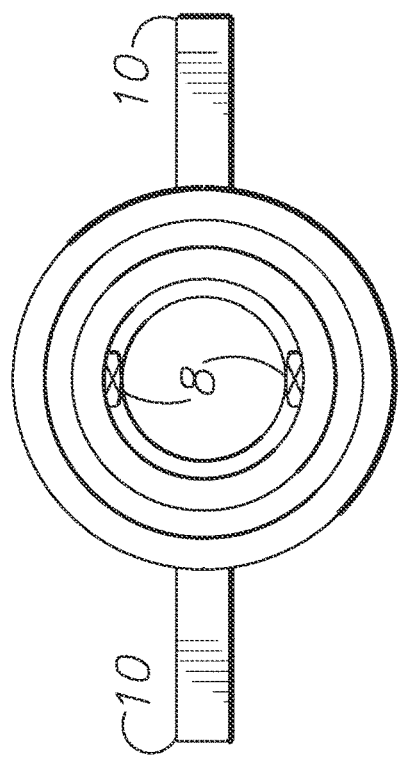
FIG. 8 is a bottom, plan view of the incisional instrument.
Figure 7:
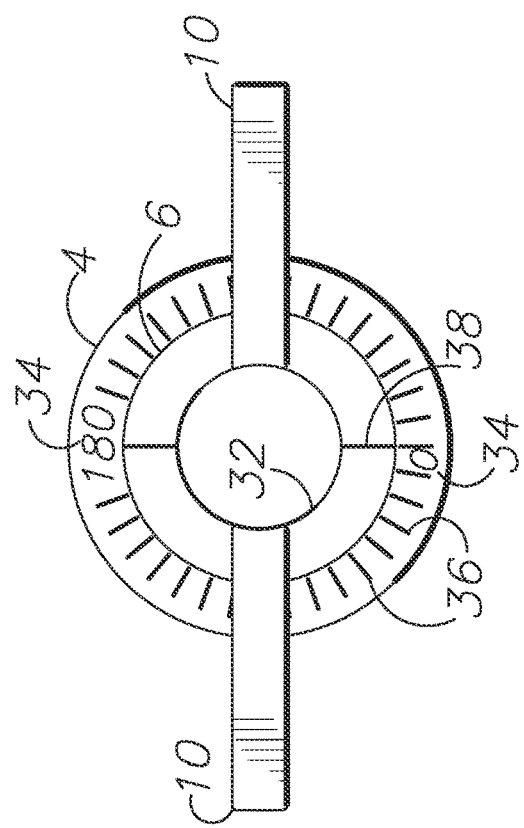
FIG. 7 is a top, plan view of the incisional instrument.
Figure 9:
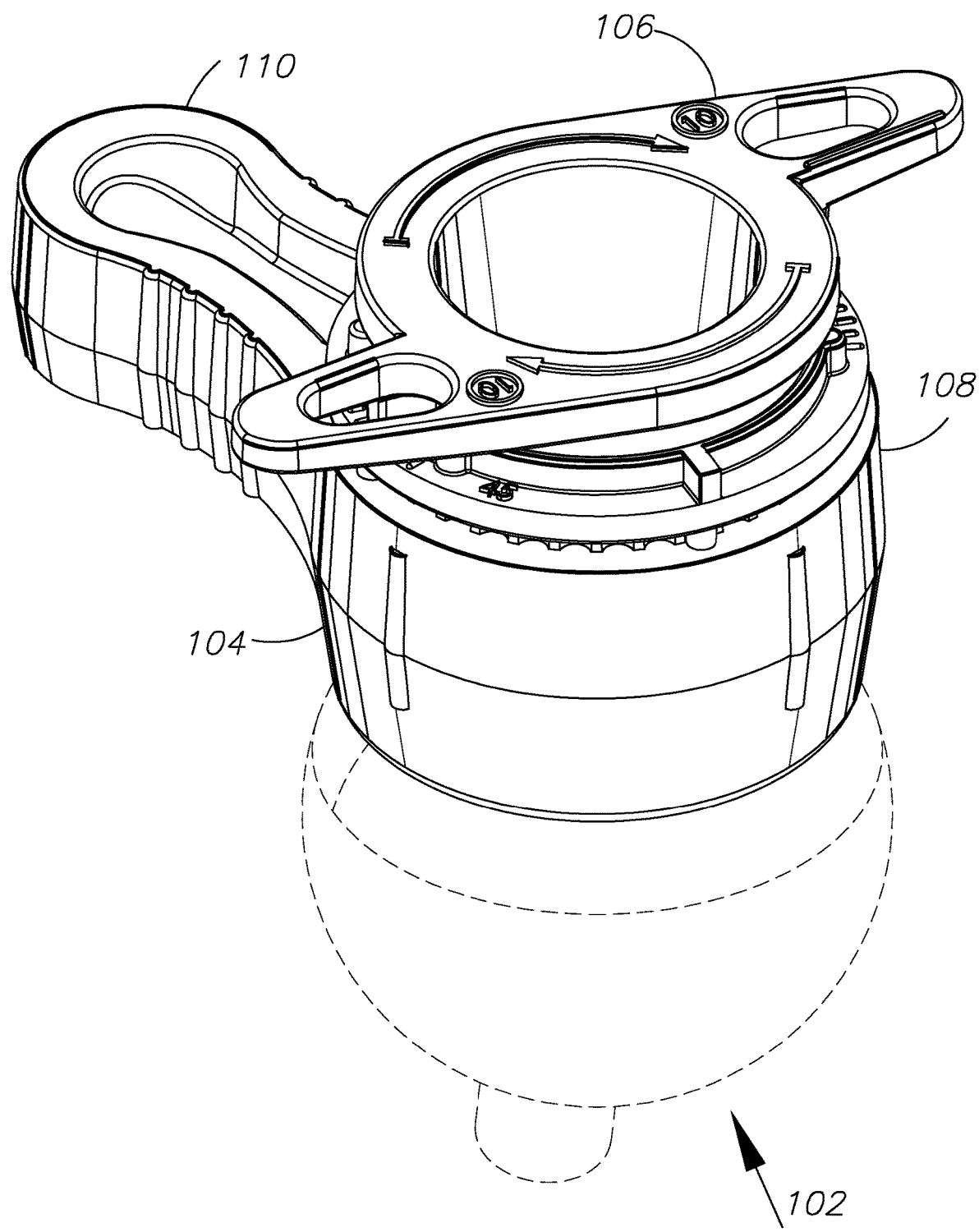
FIG. 9 is an upper, perspective view of a modified incisional instrument comprising a first alternative embodiment of the present invention.
Figure 10:
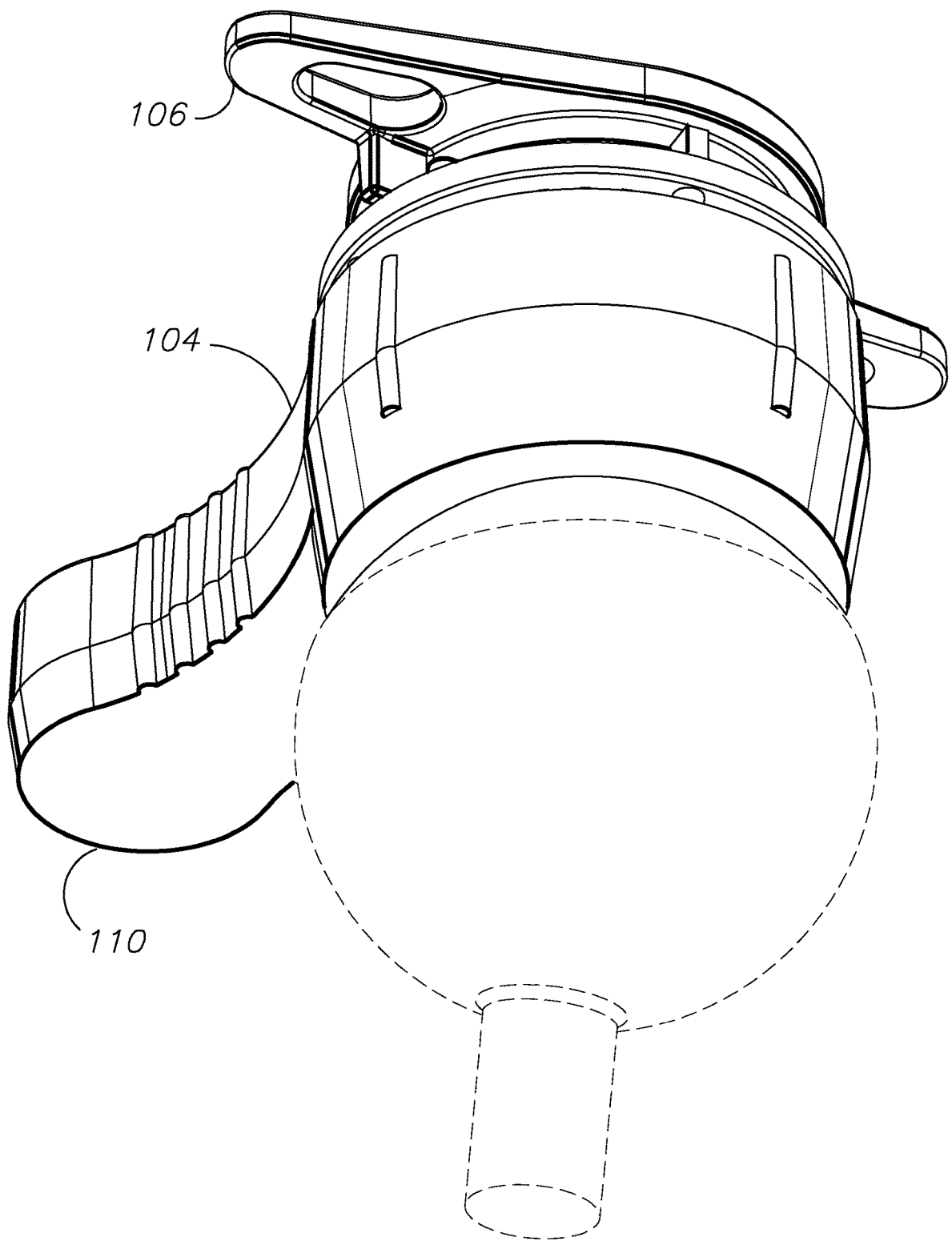
FIG. 10 is a lower, perspective view thereof.
Figure 12:
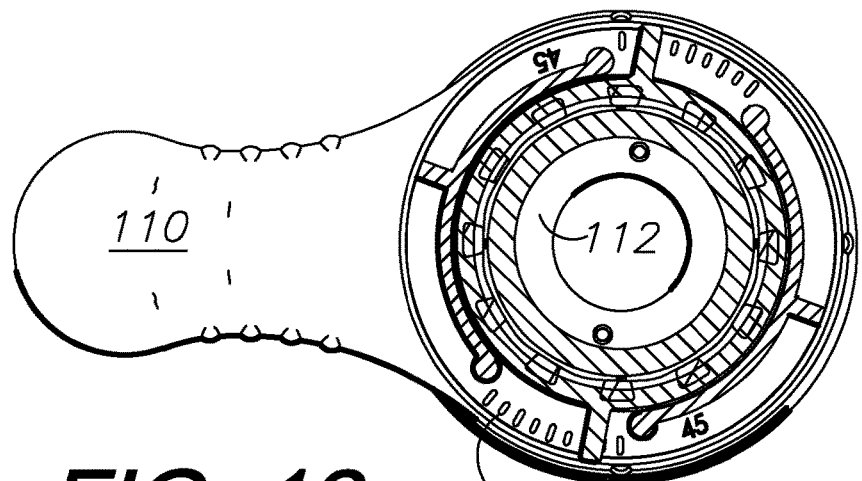
FIG. 12 is a horizontal, cross-sectional view taken generally along line 12-12 in FIG. 11.
Figure 11:
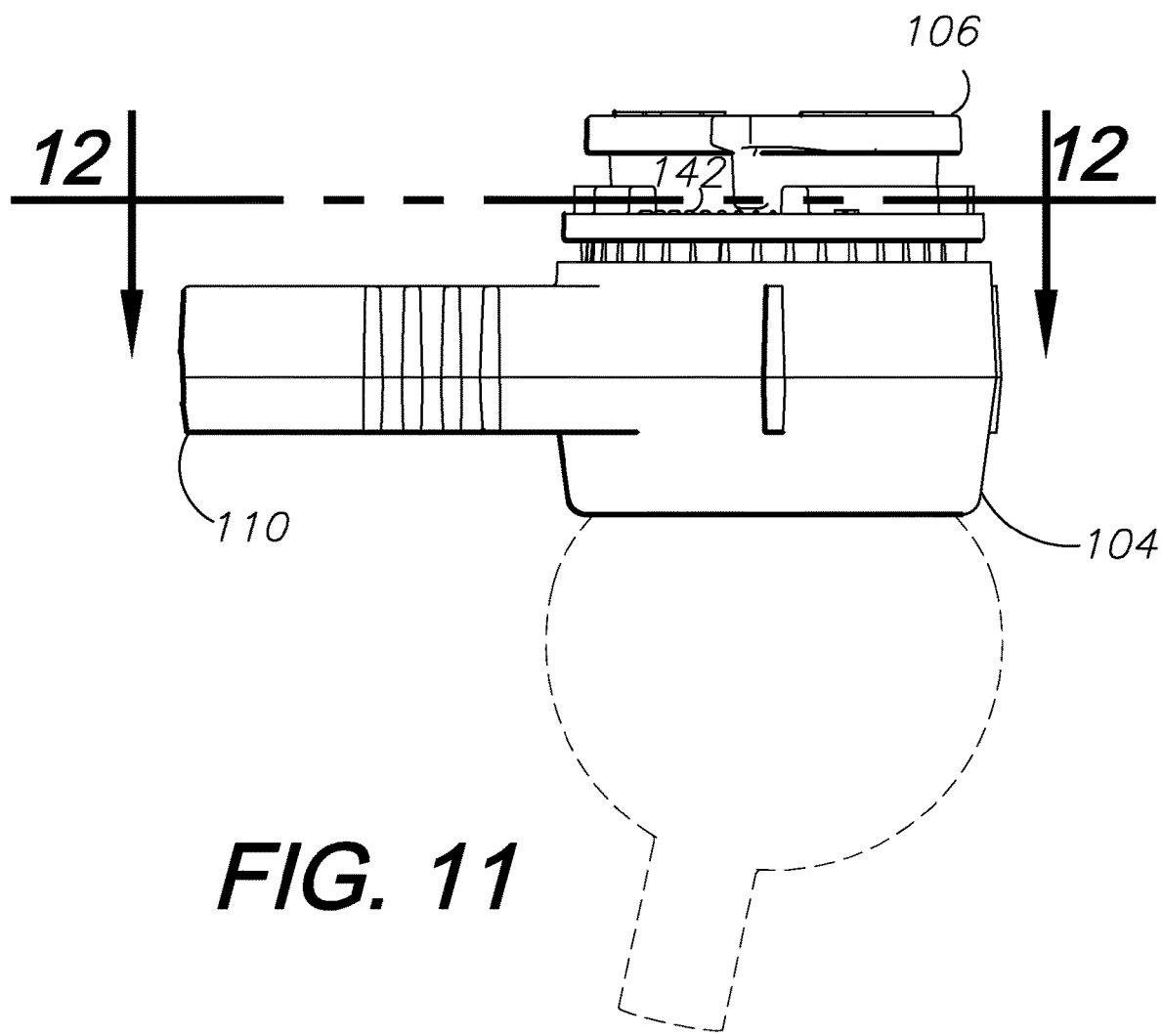
FIG. 11 is a side elevational view thereof.
Figure 13:
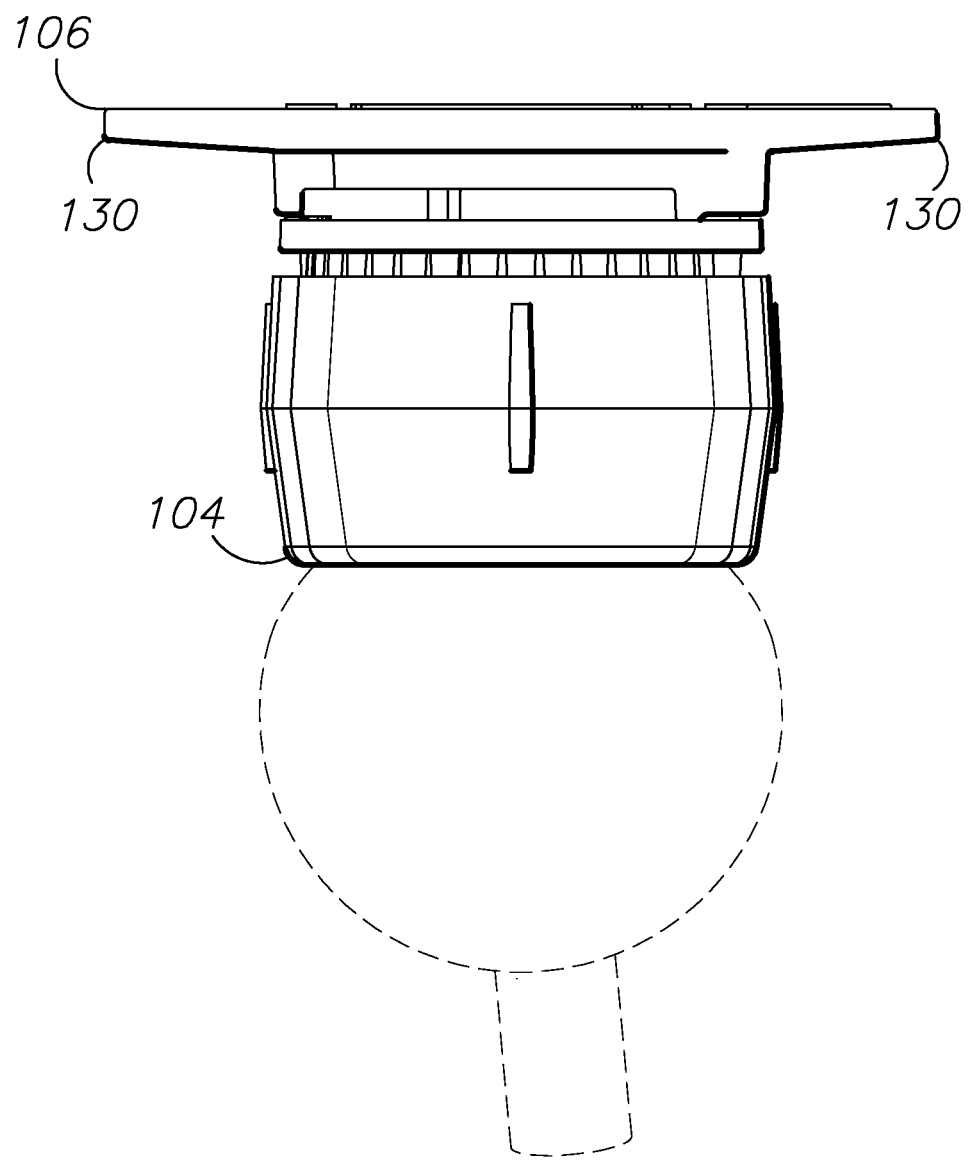
FIG. 13 is a distal end elevational view.
Figure 14:
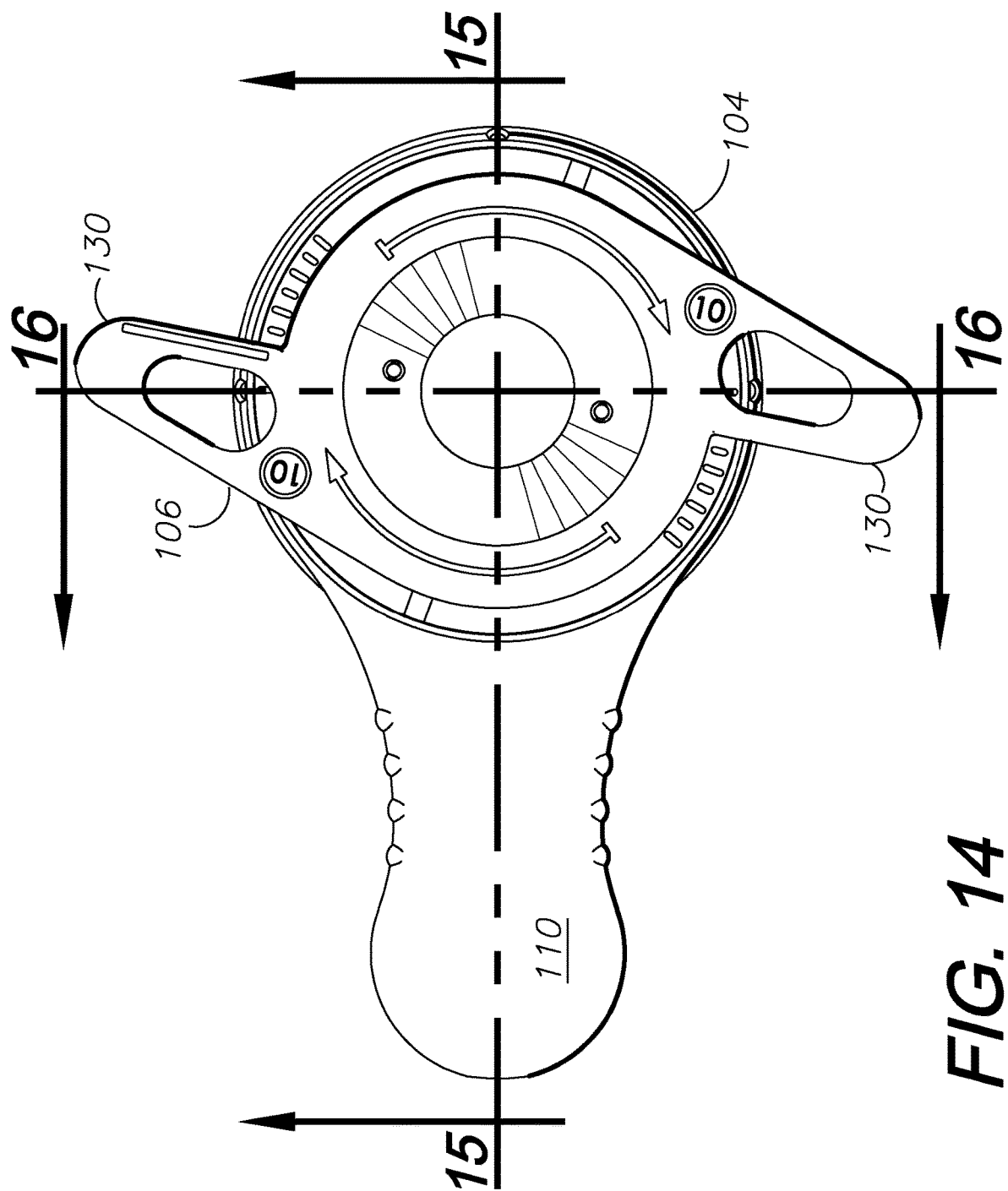
FIG. 14 is a top plan view thereof.
Figure 16:
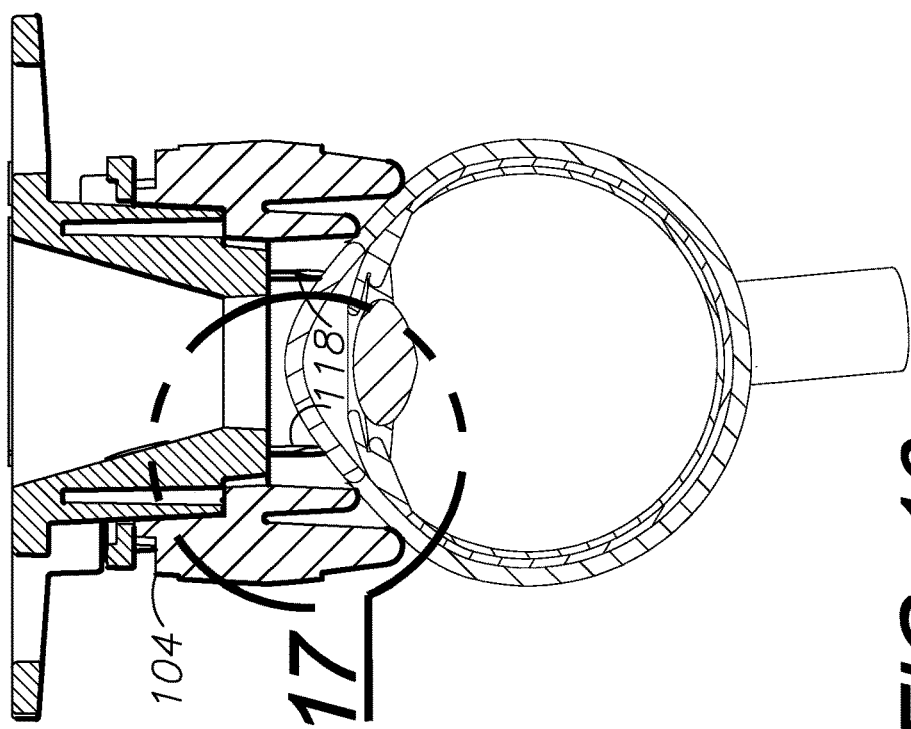
FIG. 16 is a cross-sectional view thereof, taken generally along line 16-16 in FIG. 14.
Figure 15:
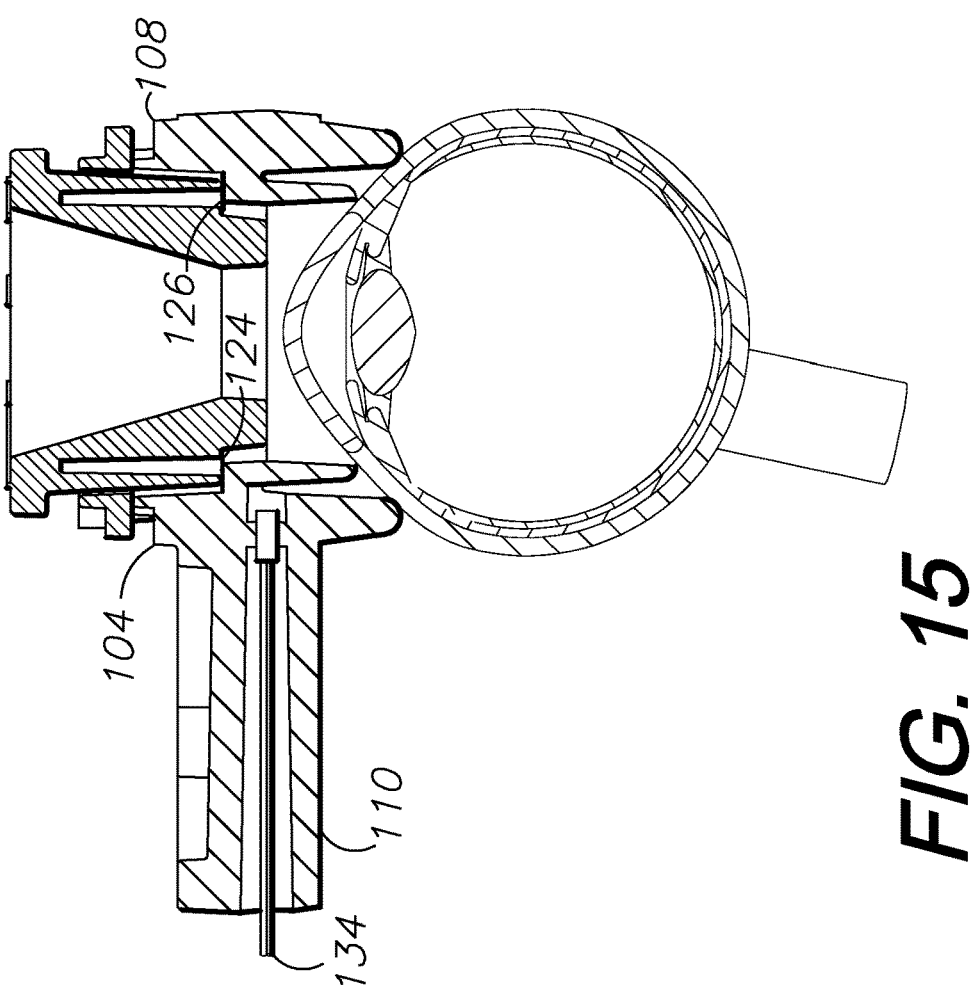
FIG. 15 is a cross-sectional view thereof taken generally along line 15-15 in FIG. 14.
Figure 18:
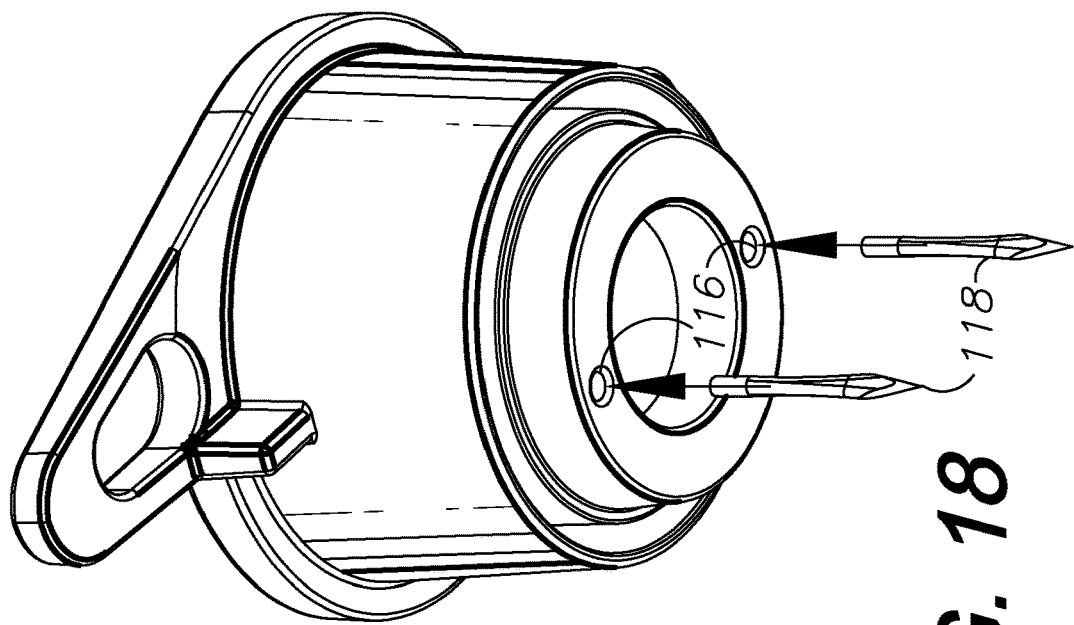
FIG. 18 is a fragmentary, bottom perspective view thereof, showing a cutting ring assembly with the incision blades extracted.
Figure 17:
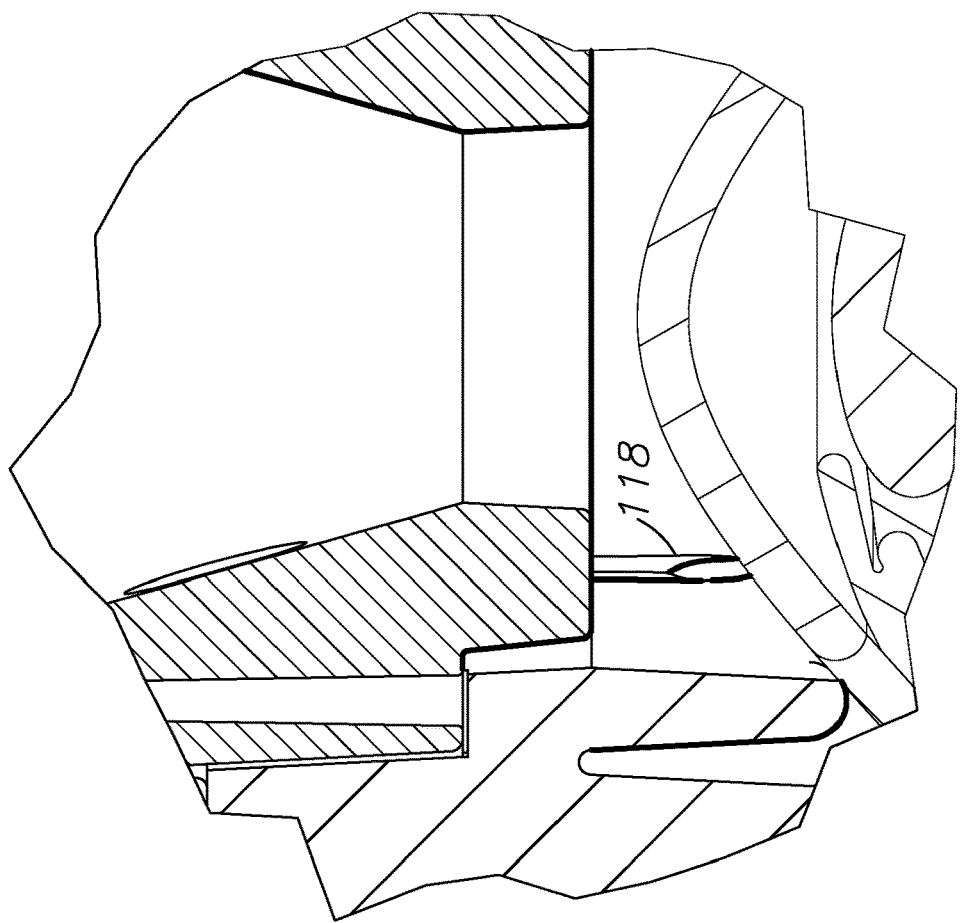
FIG. 17 is an enlarged, cross-sectional view thereof, taken generally in circle 17 in FIG. 16.

FIG. 7 shows a top, plan view of the incisional instrument 2. FIG. 7 illustrates the open center 32 of the cutting piece 6, the measurement markings 36 on the docking piece 4, and the reference markings 38 on the cutting piece 6, with the handles 10 offset by 90 degrees from the reference markings 38. FIG. 7 further illustrates reference rotational indicia 34. In this embodiment, the measurement markings 36 and rotational indicia 34 represent degrees from 0 to 360 degrees. FIG. 8 is a bottom, plan view of the incisional instrument 2. FIG. 8 shows the open center 32 of the cutting piece 6. FIG. 8 further shows the open proximal end of the suction chamber 14 of the docking piece 4, which is configured for attachment to a patient's eye 42. The cutting blades 8 are mounted from the cutting piece 6. In this embodiment, the handles 10 are radially spaced from the locations of the cutting blades 8 by approximately 90 degrees relative to the axis 12 by 90°, although other cutting blade and handle configurations, spacings and multiples are within the scope present invention.

III. First Alternative Embodiment Ophthalmic Incisional Instrument 102

An ophthalmic incisional instrument 102 for making a limbal relaxing incision (LRI) embodying a first modified or alternative embodiment of the present invention is shown in FIGS. 9-20. The instrument 102 includes a docking piece 104 and a cutting piece 106. The docking piece 104 includes a generally cylindrical main body 108 and a docking piece lever 110 extending laterally. The main body 108 of the docking piece 104 includes a coaxial bore 112, which rotatably receives the cutting piece 106.

The cutting piece 106 includes a proximal end 114 with a pair of blade receivers 116 open thereat. A pair of blades 118 each includes a shaft 120 received in a respective receiver 116. Each blade includes a proximal, sharpened, cutting end 122. The blade ends 122 are configured for forming LRIs. The docking piece 104 and the cutting piece 106 include depth-stop shoulders 124, 126, respectively. In operation, the cutting piece shoulder 126 engages and rotatably slides on the docking piece shoulder 124. The limbal penetration of the blade cutting tips 122 is thus controlled for purposes of optimizing LRI procedure outcomes.

Figure 19:
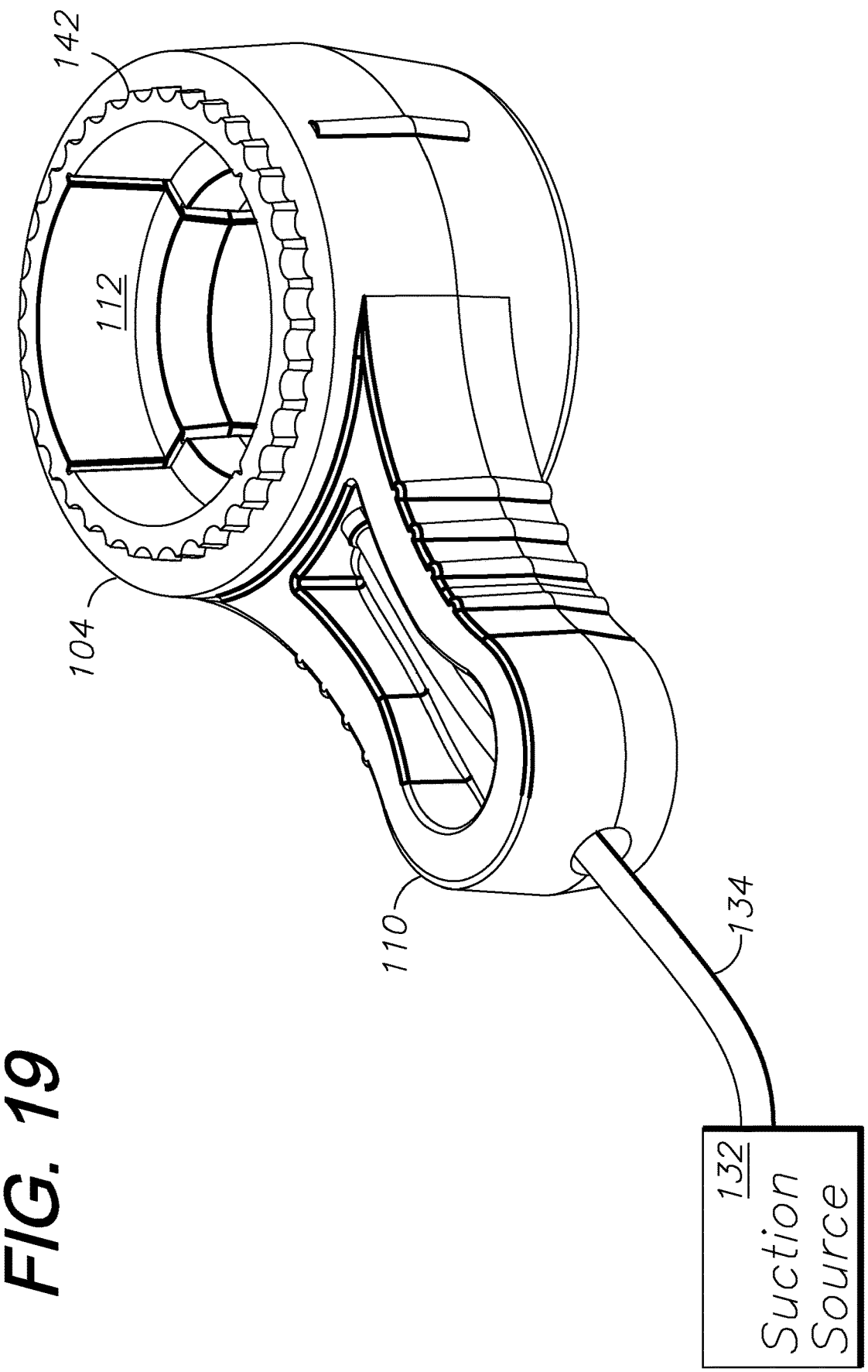
FIG. 19 is an upper, perspective view of a docking piece, shown connected to a suction source.
Figure 21:
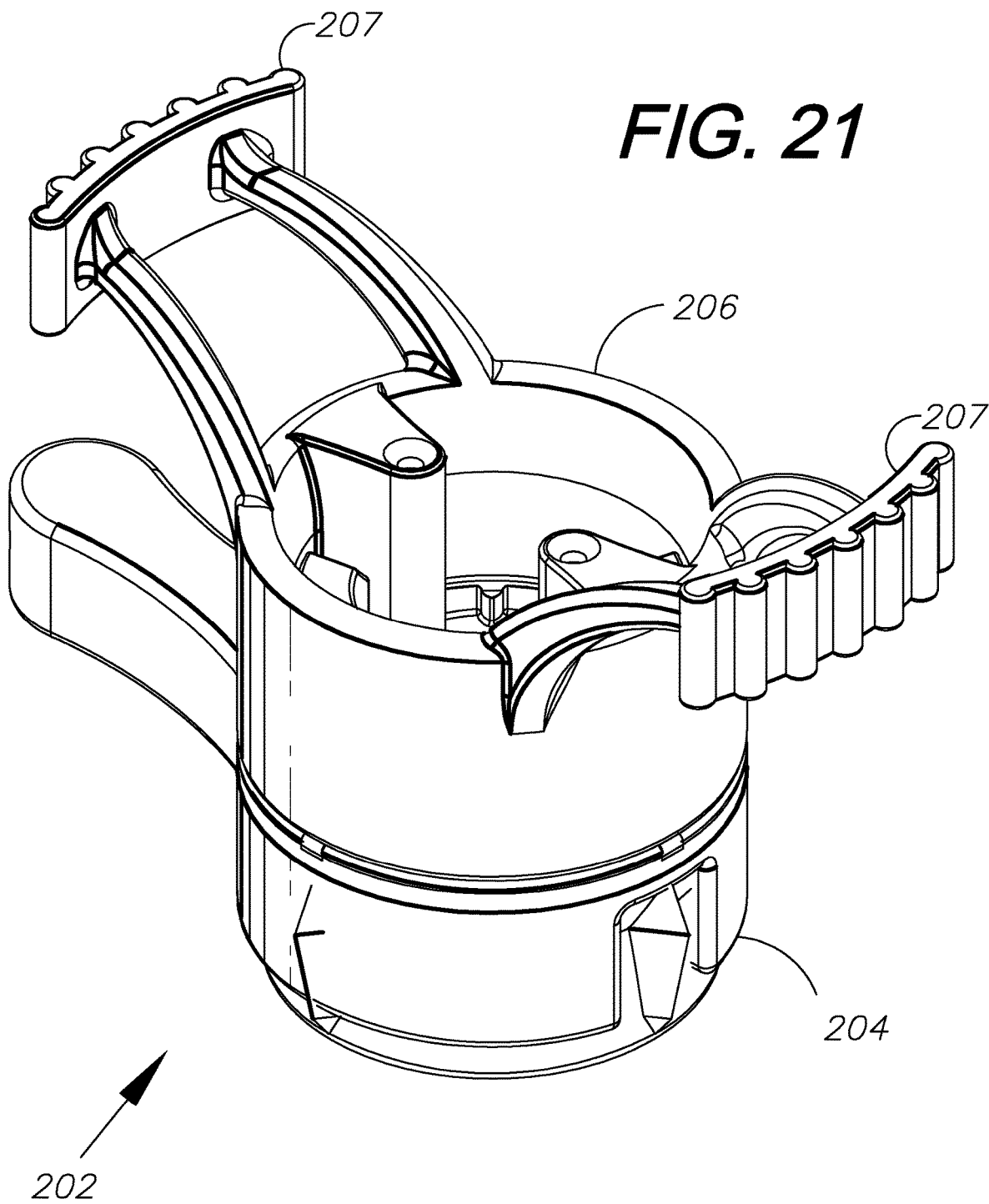
FIG. 21 is an upper, perspective view of a modified incisional instrument comprising a second alternative embodiment of the present invention.
Figure 22:
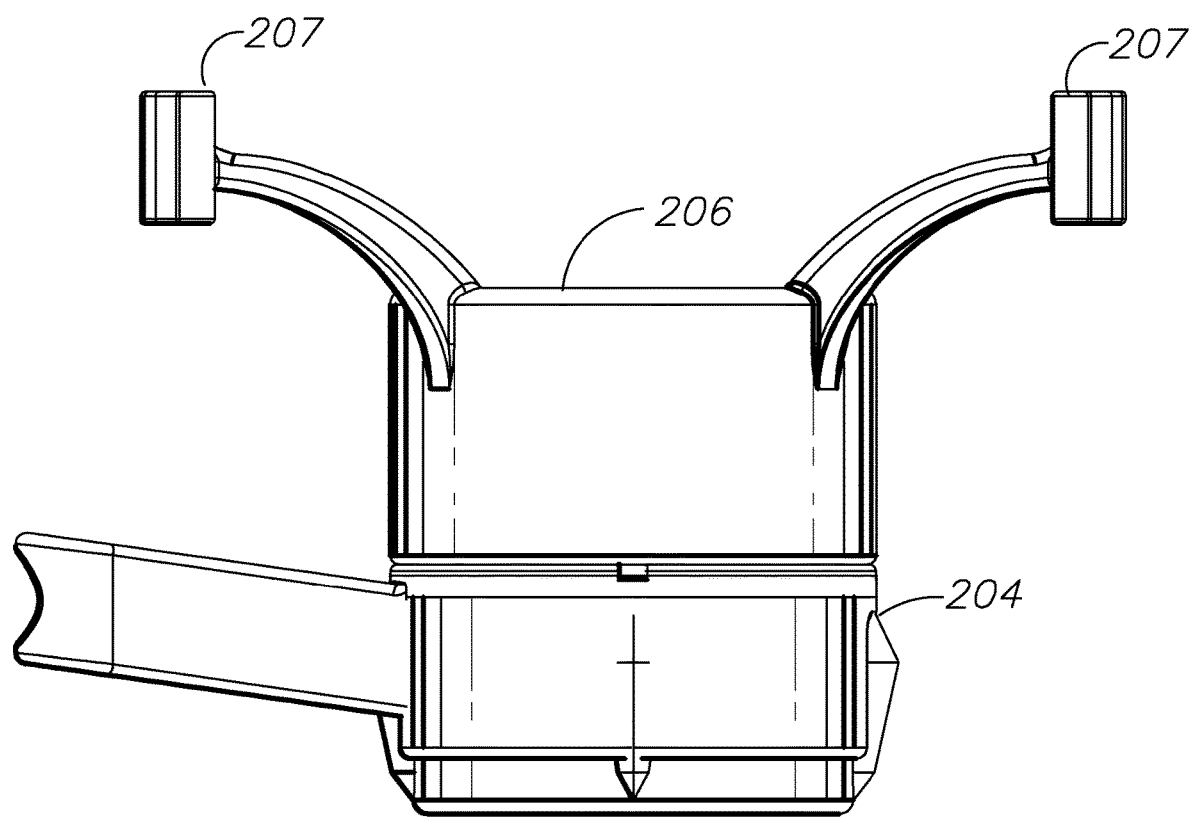
FIG. 22 is a side elevational view thereof.
Figure 23:
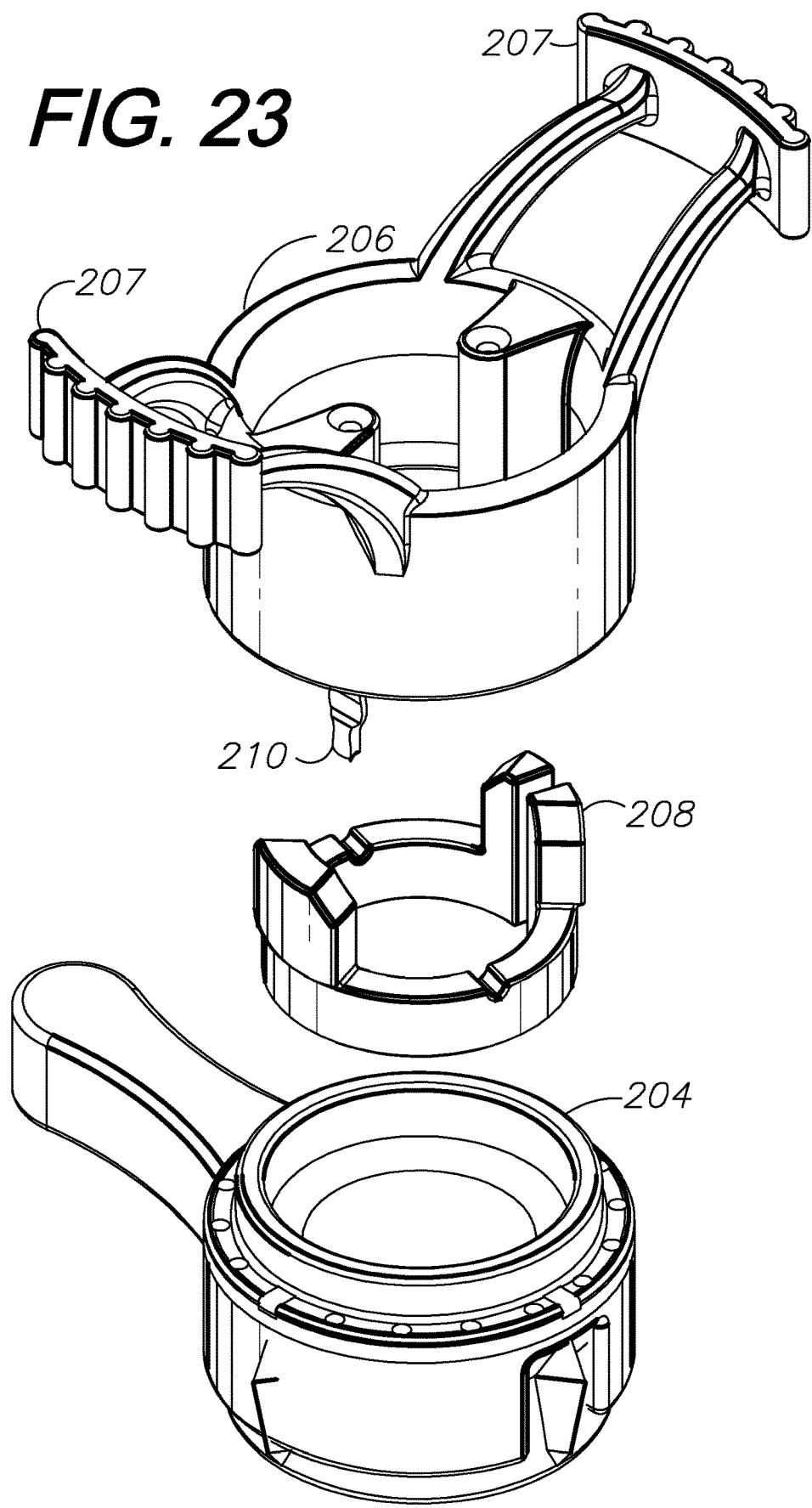
FIG. 23 is an exploded, upper perspective view thereof.
Figure 24:
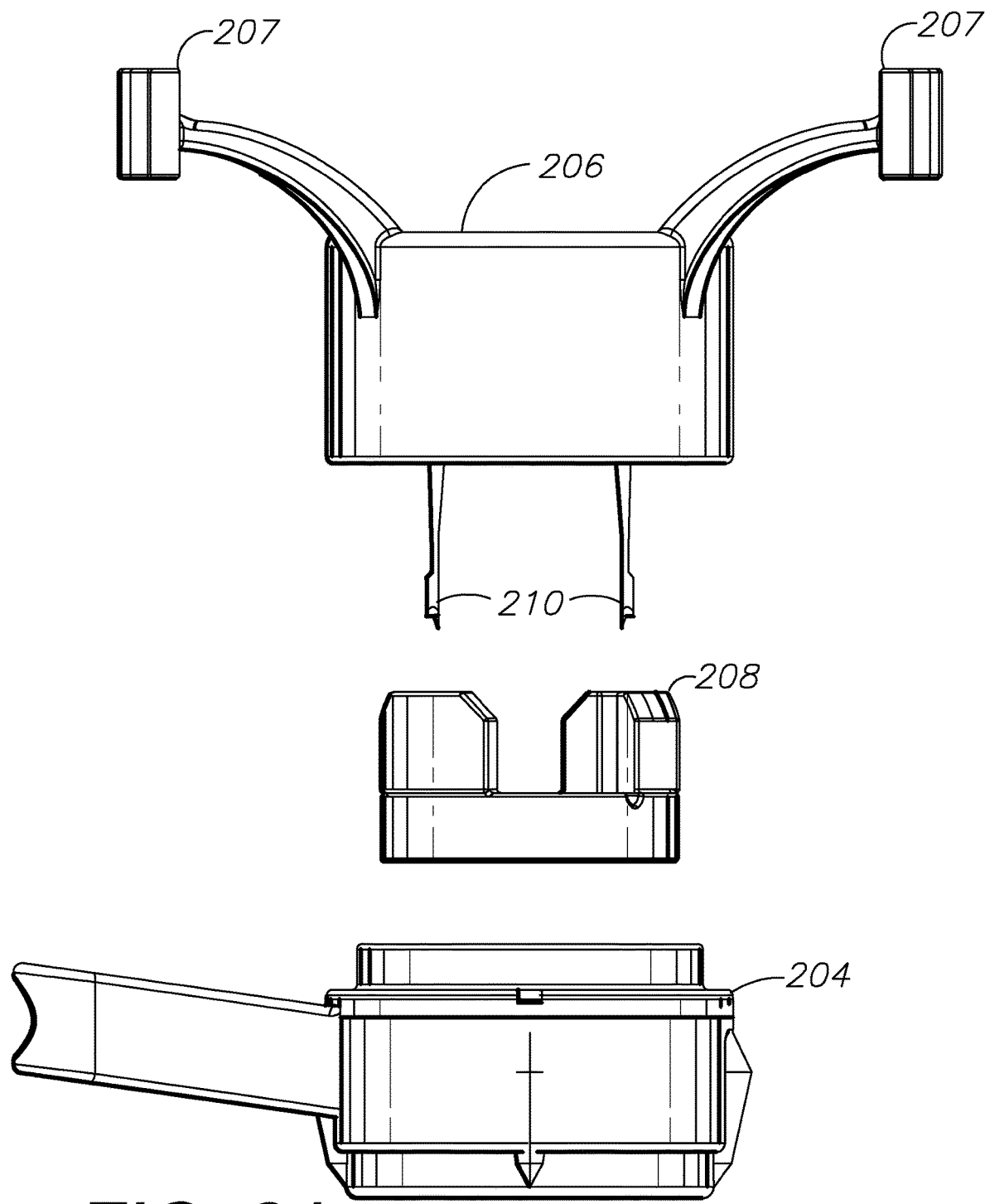
FIG. 24 is an exploded, side elevational view thereof.

The cutting piece 106 further includes a distal end 128 with a pair of laterally-extending cutting piece levers 130. A physician can conveniently position the docking piece 104 on a patient's cornea by grasping the docking piece lever 110. As shown in FIG. 19, a suction source 132 can be connected to the docking piece 104 via suction tubing 134. A negative pressure partial vacuum can be exerted for securing the docking piece 104 in place on a patient's cornea. Similar to the ophthalmic incisional instrument 2 described above, the docking piece 104 is configured for releasable attachment to a patient's eye by suction (negative pressure). The ophthalmic incisional instrument 102 includes a coaxial, arcuate guide template 136 configured for attachment to the docking piece and for providing arcuate mechanical stops for the cutting piece 106 in an assembled configuration. The arcuate guide template 136 is configured to provide added safety and precision for LRI procedures by preventing lateral rotation of the cutting piece beyond the designated incision areas for the cutting blades 118.

Another safety feature comprises a blade safety 138, which includes a generally cylindrical configuration and multiple, radially-spaced, distally-open notches 140. The docking and cutting pieces 104, 106 include detents 142 engageable by other elements for making fine adjustments (e.g., 5°-10°). Arcuate guide templates 136 can be provided for multiple LRI arc lengths. For example, the guide template 136 shown in FIGS. 11 and 12 form 45° LRI arcs, as defined by the rotational range of motion of the docking piece 104 relative to the cutting piece 106. Moreover, the components and templates of the LRI instruments can be provided with suitable internal marks and reticles to help with alignment on patients' eyes for relatively precise and accurately-placed arcuate incisions.

IV. Second Alternative Embodiment Ophthalmic Incisional Instrument 202

A second alternative embodiment instrument 202 is shown in FIGS. 21-24. The instrument 202 generally includes a docking piece 204 and a cutting piece 206. A guide template 208 is provided for controlling the rotation of the docking piece 204 relative to the cutting piece 206. A pair of grips 207 extend from the cutting piece 206 and enable manual rotation of the cutting piece 206. A pair of blades 210 are mounted in and depend downwardly from the cutting piece 206.

V. Third Alternative Embodiment Ophthalmic Incisional Instrument 302

Figure 25:
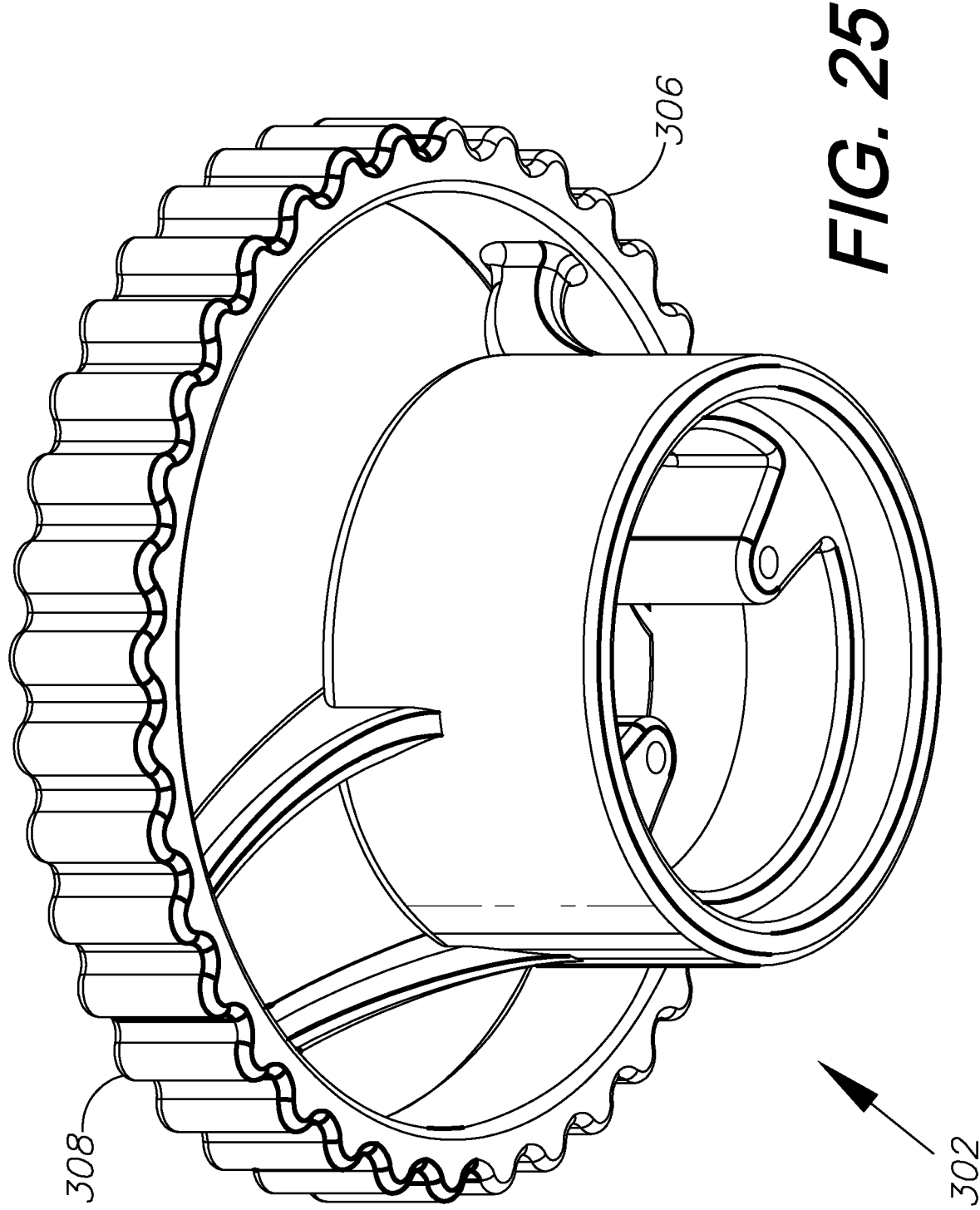
FIG. 25 is a lower, perspective view of an ophthalmologic LRI instrument comprising a third modified or alternative embodiment of the present invention.
Figure 26:
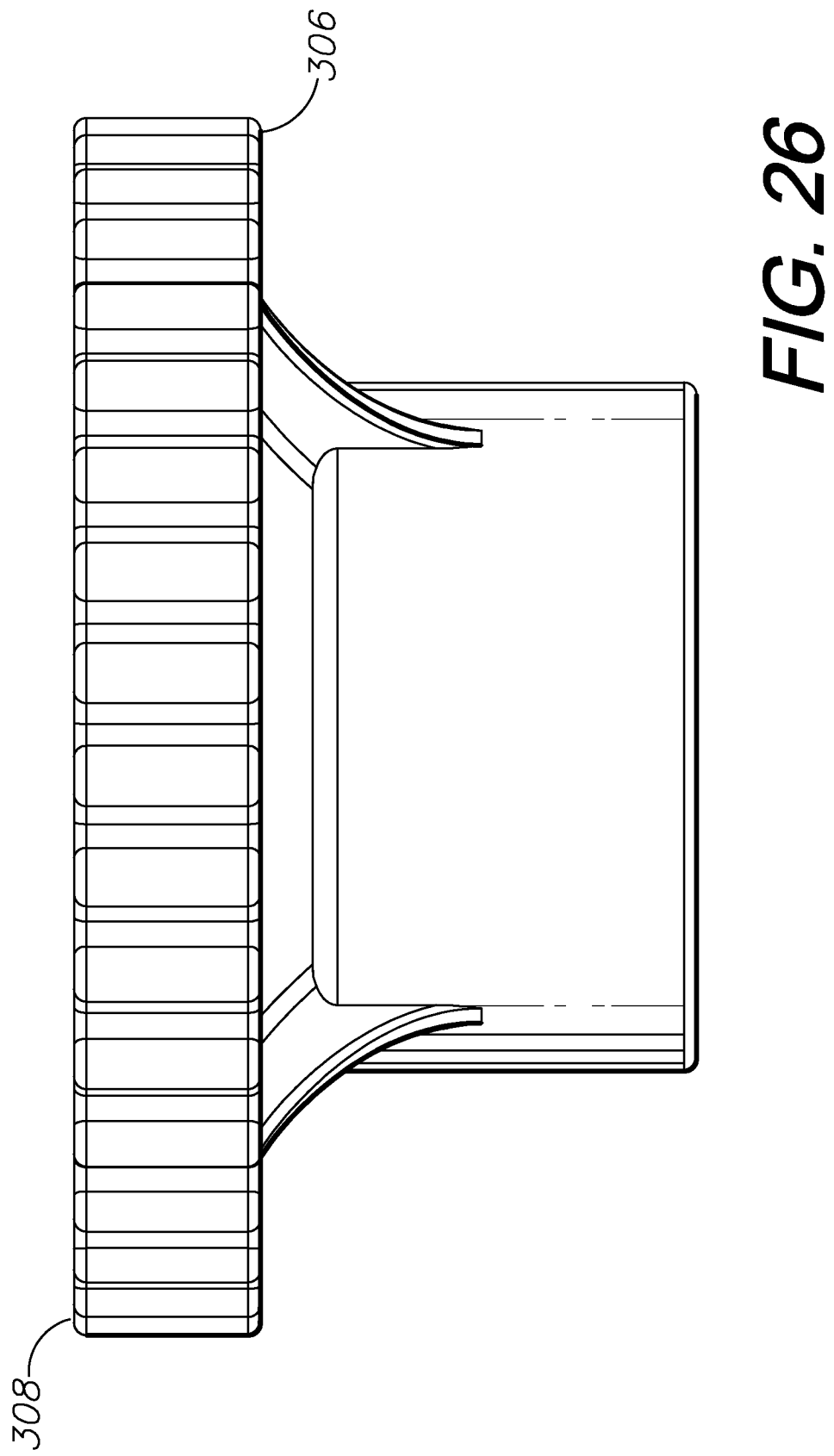
FIG. 26 is a side elevational view thereof.
Figure 27:
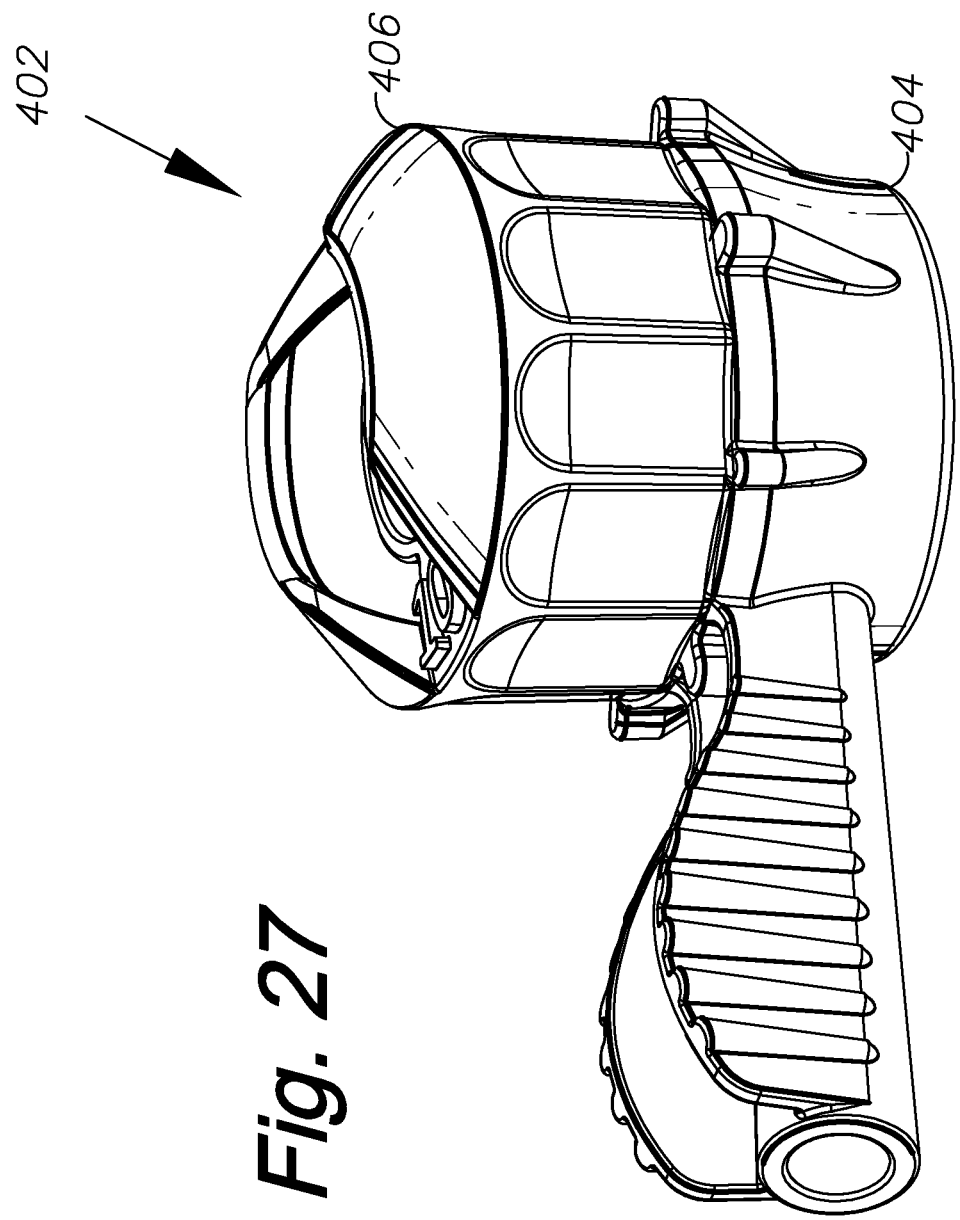
FIG. 27 is an upper, perspective view of an ophthalmologic LRI instrument comprising a fourth modified or alternative embodiment of the present invention.
Figure 28:
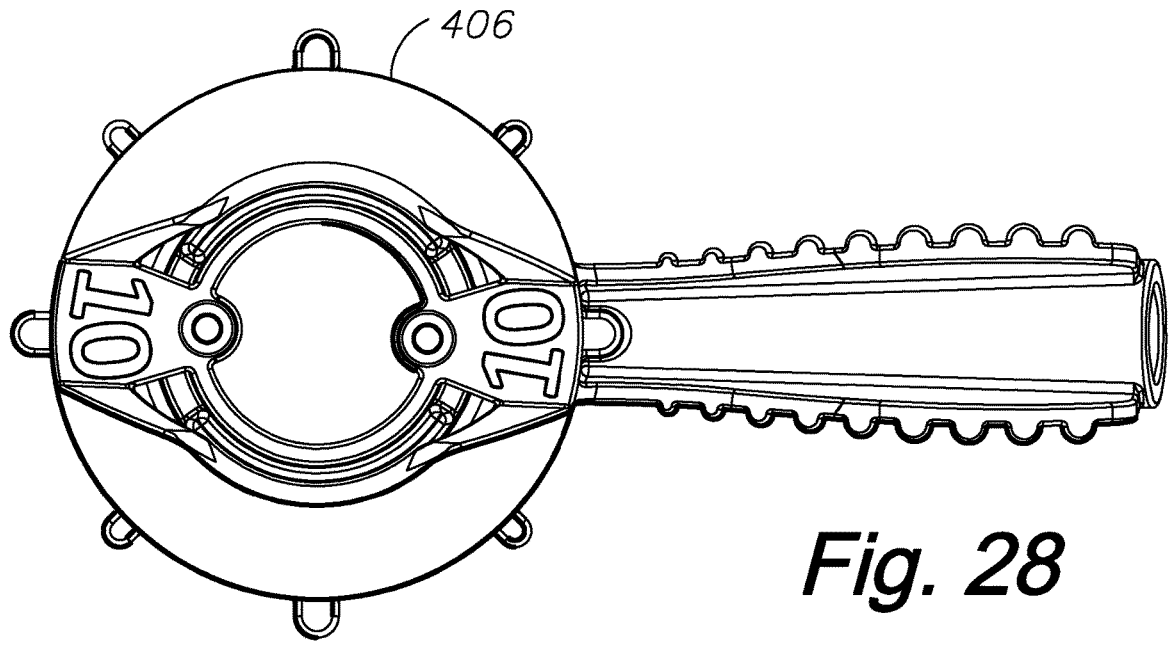
FIG. 28 is a top plan view thereof.
Figure 29:
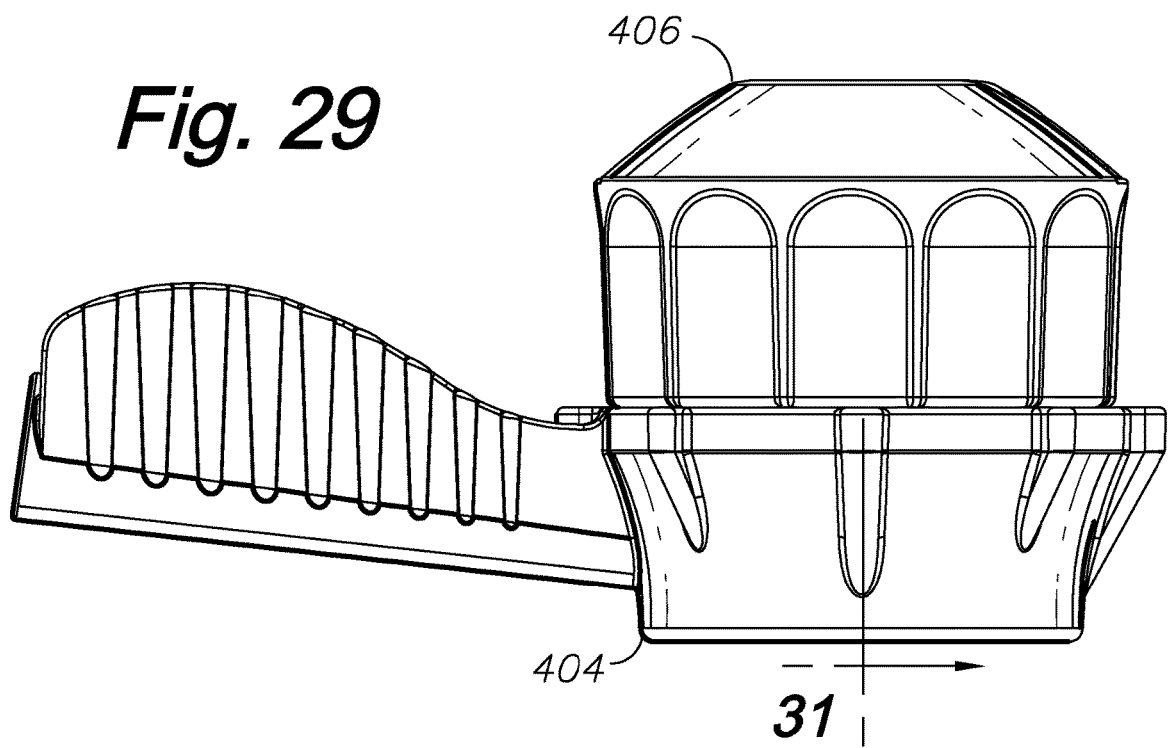
FIG. 29 is a side elevational view thereof.
Figure 30:
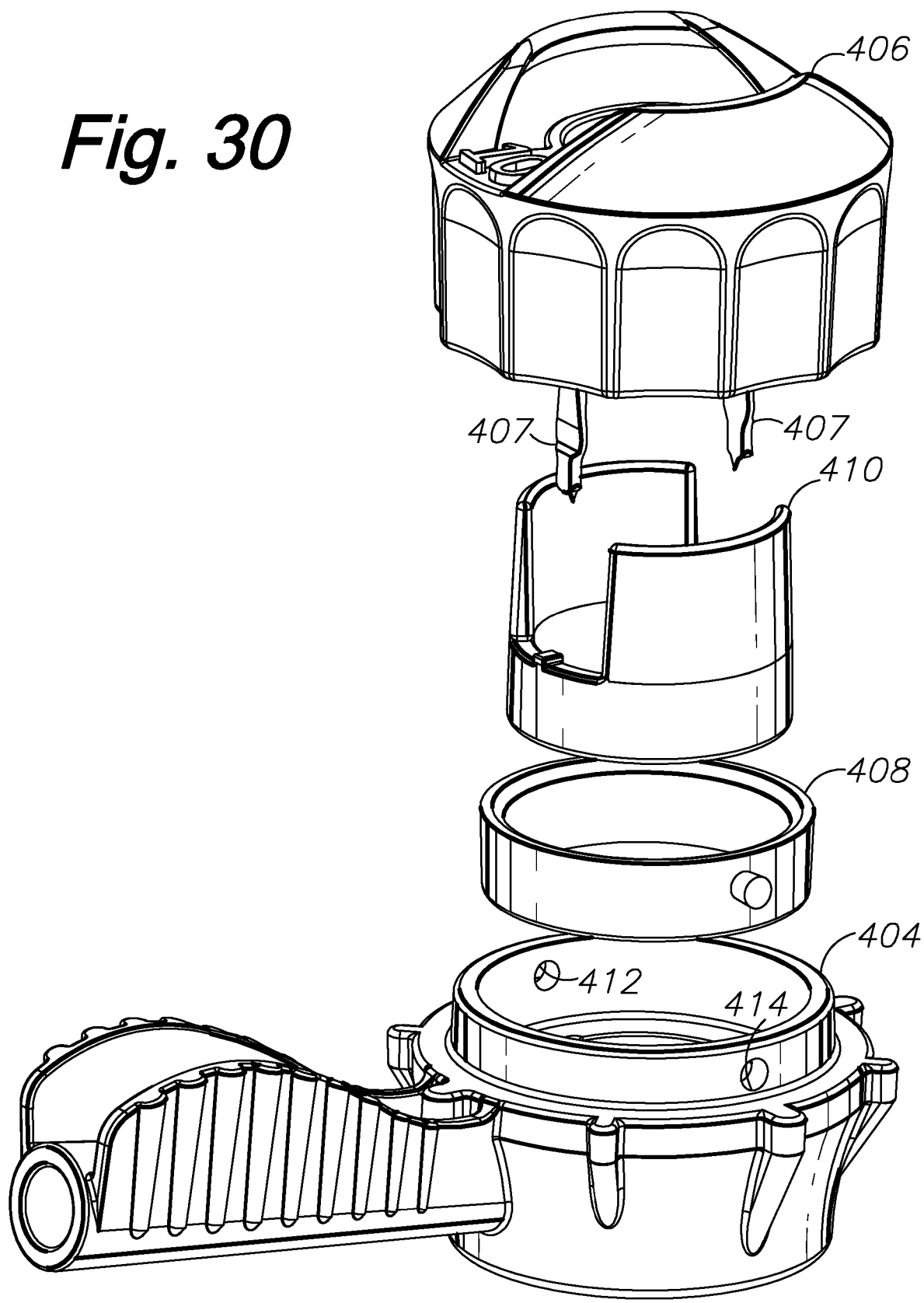
FIG. 30 is an exploded, perspective view thereof.
Figure 31:
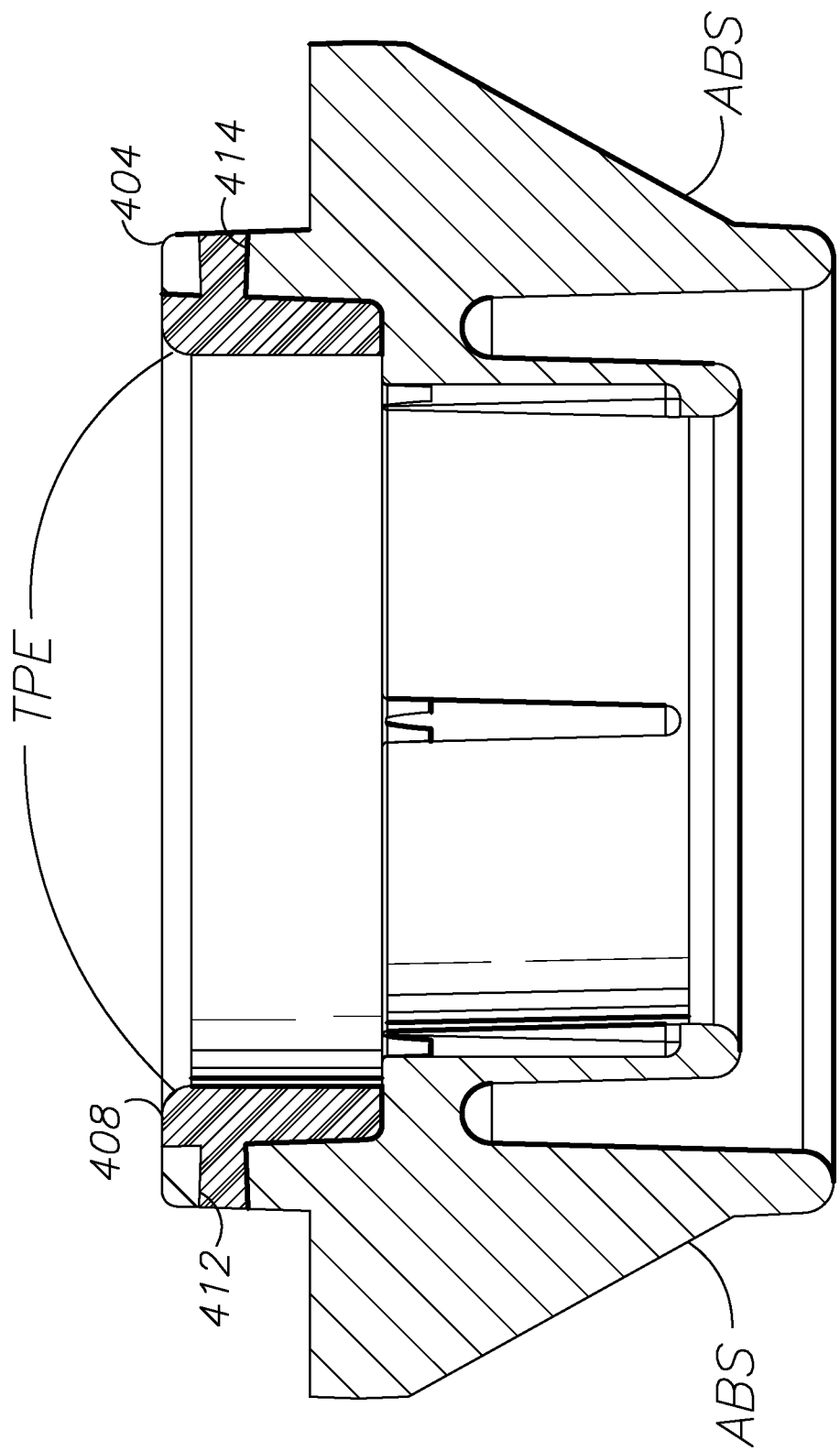
FIG. 31 is a cross-sectional view of the docking piece and a distal spacer or template mounted thereon, taken generally along section line 31 in FIG. 29.

A third alternative embodiment instrument 302 is shown in FIGS. 25-26 and includes a cutting piece 306 with a cylindrical grip ring 308. The instrument 302 is otherwise structurally and functionally similar to the instruments 2, 102 and 202 described above.

VI. Fourth Alternative Embodiment Ophthalmic Incisional Instrument 402

A fourth alternative embodiment instrument 402 is shown in FIGS. 27-31 and generally includes a docking piece 404 and a cutting piece 406 mounting a pair of proximally-extending blades 407. A proximal spacer 408 is received in the docking piece 404. A distal spacer 410 is received in the proximal spacer 408 and in the cutting piece 406.

Without limitation on the generality of useful materials for fabricating the incisional instrument 402, a thermoplastic polymer, such as acrylonitrile butadiene styrene (ABS) can be used for the docking piece 404, the cutting piece 406 and the distal spacer or template 410. The ABS components can be formed by injection molding. The proximal spacer 408 can comprise a thermoplastic elastomer (TPE), which is softer and more flexible than the ABS plastic.

The proximal spacer 408 can be formed by overmolding the docking piece 404. TPE elastomer is injected through a gate opening 412 and exits through an overflow opening 414. The openings 412 and 414 are sealed by the TPE material in the finished spacer 408. The proximal spacer 408 provides proper mating and friction fit of the distal spacer or template 410, which is seated in the pocket formed by the proximal spacer 408. The template 410 is allowed to rotate, but with slight resistance due to the greater coefficient of friction with the TPE material, which can prevent inadvertent rotational movement during an LRI procedure.

Similar production techniques and material choices can be utilized for the other LRI embodiments disclosed herein. For example, various polymers can be used for forming the components by injection molding and other suitable processes.

VII. Limbal Relaxation Incision (LRI) Procedures

The ophthalmic incision instruments, 2, 102, 202, 302 and 402 disclosed herein can be provided with axis alignment markings for added ease of properly and precisely aligning the ophthalmic incisional device on a patient's eye for an LRI procedure. In a preferred embodiment, the docking piece of the present invention includes markings representing the x-axis and y-axis of the patient's eye to be cut. Such x-axis and y-axis markings on the docking piece can then be matched up with the x-axis and y-axis of the patient's eye to be operated on, respectively, prior to releasable attachment via suction of the docking piece to the patient's eye to aid in precise alignment. The x-axis and y-axis may be initially marked on the patient's eye with a marking pen, if desired, prior to placing the docking piece, or alternative alignment tools or computing devices may be utilized. In embodiments of the present invention, the docking piece may include alternative or additional markings for alignment with the eye, such as but not limited to degrees, radians, gradians, revolutions, or any other units of measurement of an angle.

Once the docking piece is properly placed on the patient's eye, alignment markings on the arcuate guide template can be used to precisely align the arcuate guide template in relation to the docking piece and the x-axis and y-axis of the patient's eye as desired for the LRI procedure to be conducted. For example, an ophthalmologist using the present ophthalmic incisional device may use a nomogram to determine the cut positions for an LRI procedure. Based on the relevant nomogram reading, the user can align the axis alignment markings in relation to the horizontal axis of the patient's eye and docking piece as desired for the particular LRI procedure. Alternatively, other alignment or prediction tools and/or anatomical modeling software may be utilized in determination of LRI cut locations and size and positioning of the arcuate guide template in relation to the docking piece.

The arcuate guide template and docking piece of the present invention can optionally further include a locking mechanism for locking the arcuate guide template in place in relative position to the docking piece. Such a locking mechanism can comprise a telescoping clamp, a pin and associated grooves, a locking button, or any other type of locking mechanism.

As discussed above, the docking and cutting piece levers enable manual positioning of the LRI instruments. Preferably, the docking piece levers have ergonomic shapes facilitating grasping and holding docking pieces. y be any shape.

The docking piece levers also provide enclosures for vacuum tubing connecting docking piece suction chambers to a vacuum devices such as a syringes and automated, pneumatic suction pumps. Such a base handle housing for vacuum tubing holds the tubing properly in place and helps to keep the vacuum tubing out of the way of the LRI procedure while also helping to prevent the vacuum tubing from unintentionally being pulled away from the docking piece suction chamber during the LRI procedure. The vacuum tubing may connect to the suction chamber via a Luer lock connection, an O-ring connection, or an alternative sealed connection.

It is to be understood that the invention can be embodied in various forms and is not to be limited to the examples specifically discussed above. The range of components and configurations which can be utilized in the practice of the present invention is virtually unlimited.

Having thus described the invention, what is claimed as new and desired to be secured by Letters Patent is:

1. An ophthalmic incisional instrument for making limbal relaxing incisions (LRIs) on a patient's eye having a sclera, a cornea, and a corneal limbus, the instrument comprising:
a docking piece having proximal and distal ends;
said docking piece proximal end configured for placement on the sclera of said patient's eye;
a cutting piece having proximal and distal ends and a rotational axis extending between said cutting piece ends;
said cutting piece configured for insertion within said docking piece and for rotation relative to said docking piece about said rotational axis in an assembled configuration of the instrument;
said cutting piece mounting two cutting blades, each cutting blade configured for extending into said patient's eye in said assembled configuration;
a guide template having proximal and distal ends;
said guide template proximal end configured for attachment to said docking piece distal end in said assembled configuration;
said guide template distal end comprising raised stoppers configured for providing lateral, arcuate stops for said cutting piece in said assembled configuration preventing rotation of said cutting piece beyond desired LRI locations;
said docking piece further comprising a step portion configured for providing a mechanical stop for said cutting piece in said assembled configuration preventing further extension of said cutting blades into said patient's eye beyond a desired LRI depth of cut;

said docking piece further comprising a suction chamber open at said docking piece proximal end;

wherein said docking piece is configured for releasable attachment to the sclera of said patient's eye via sub-atmospheric pressure in said suction chamber; and said cutting blades configured for forming arcuate LRIs in said patient's eye coaxial to said rotational axis wherein said cutting piece further comprises an open center accommodating visualization of said LRIs, and wherein said docking piece further comprises axial alignment markings; and said guide template further comprises reference markings for alignment in relation to said docking piece.

2. The incisional instrument according to claim 1, wherein:

said docking piece further comprises an open center accommodating alignment of said docking piece on said sclera of said patient's eye.

3. The incisional instrument according to claim 1, wherein:

said docking piece further comprises an opening to said suction chamber; and said suction chamber opening is configured for sealable attachment to a sub-atmospheric pressure source.

4. The incisional instrument according to claim 3, wherein:

said docking piece further comprises a base handle;

said base handle comprises a housing;

said suction chamber opening connects to said base handle housing; and said base handle housing is configured for housing tubing connecting said suction chamber to said sub-atmospheric pressure source.

5. The incisional instrument according to claim 1, wherein:

said cutting blades are positioned in 180-degree opposed relation; and said cutting blades are configured for making symmetrical incisions of equal length, depth, and curvature.

6. The incisional instrument according to claim 1, wherein:

said cutting piece further comprises a handle on said cutting piece distal end; and said handle accommodates efficient rotation of said cutting piece relative to said docking piece.

7. The incisional instrument according to claim 1, wherein:

said cutting blades comprise depth-controlled blades for preventing perforation of said patient's eye.

8. The incisional instrument according to claim 1, wherein:

said instrument is substantially translucent and configured for absorbing surrounding light.

9. The incisional instrument according to claim 1, wherein:

said cutting blades are detachable; and said cutting blades are configured for detachment and for replacement with cutting blades of a desired alternative length.

10. An ophthalmic incisional instrument for making limbal relaxing incisions (LRIs) on a patient's eye having a sclera, a cornea, and a corneal limbus, the instrument comprising:

a docking piece having proximal and distal ends;

said docking piece proximal end configured for placement on the sclera of said patient's eye;

a cutting piece having proximal and distal ends and a rotational axis extending between said cutting piece ends;

said cutting piece configured for insertion within said docking piece and for rotation relative to said docking piece about said rotational axis in an assembled configuration of the instrument;

said cutting piece mounting two cutting blades, each cutting blade configured for extending into said patient's eye in said assembled configuration;

a guide template having proximal and distal ends;

said guide template proximal end configured for attachment to said docking piece distal end in said assembled configuration;

said guide template distal end comprising raised stoppers configured for providing lateral, arcuate stops for said cutting piece in said assembled configuration preventing rotation of said cutting piece beyond desired LRI locations;

said docking piece further comprising a step portion configured for providing a mechanical stop for said cutting piece in said assembled configuration preventing further extension of said cutting blades into said patient's eye beyond a desired LRI depth of cut;

said docking piece further comprising a suction chamber open at said docking piece proximal end;

wherein said docking piece is configured for releasable attachment to the sclera of said patient's eye via sub-atmospheric pressure in said suction chamber;

said cutting blades configured for forming arcuate LRIs in said patient's eye coaxial to said rotational axis;

said docking piece further comprises an open center accommodating alignment of said docking piece on said sclera of said patient's eye;

said docking piece, including reticle markings configured for placing and measuring the LRIs on the patient's eye;

said cutting piece further comprises an open center accommodating better visualization of said LRIs;

said docking piece further comprises an opening to said suction chamber;

said suction chamber opening is configured for sealable attachment to a sub-atmospheric pressure source;

said docking piece further comprises a base handle;

said base handle comprises a housing;

said suction chamber opening connects to said base handle housing;

said base handle housing is configured for housing tubing connecting said suction chamber to said sub-atmospheric pressure source;

said cutting blades are positioned in 180-degree opposed relation;

said cutting blades are configured for making symmetrical incisions of equal length, depth, and curvature;

said cutting piece further comprises a handle on said cutting piece distal end;

said handle accommodates efficient rotation of said cutting piece relative to said docking piece;

said docking piece further comprises axis alignment markings;

said guide template further comprises reference markings for alignment in relation to said docking piece;

said cutting blades comprise depth-controlled blades for preventing perforation of said patient's eye;

a spacer mounted on said docking piece distal end said and configured for engaging said cutting piece in a frictional relation; and said docking piece comprising a first, relatively rigid polymer and said spacer comprising a second, relatively flexible, elastomeric polymer.

11. An ophthalmic method for making limbal relaxing incisions (LRIs) on a patient's eye having a sclera, a cornea, and a corneal limbus with an incisional instrument including a docking piece having proximal and distal ends, a suction chamber open at the docking piece proximal end, and a step portion; a cylindrical cutting piece having proximal and distal ends and a rotational axis extending between the cutting piece ends; the cutting piece configured for insertion within the docking piece and for rotation relative to the docking piece about the rotational axis in an assembled configuration of the instrument; the cutting piece mounting two cutting blades; a guide template having proximal and distal ends; the guide template proximal end configured for attachment to the docking piece distal end in the assembled configuration; and the guide template distal end comprising raised stoppers and said docking piece further comprises axis alignment markings, and said guide template further comprises reference markings for alignment in relation to said docking piece; the method comprising the steps of:

aligning said docking piece proximal end on the sclera of said patient's eye;

applying sub-atmospheric pressure to said suction chamber, attaching said docking piece to said sclera of said patient's eye; and aligning said guide template with said docking piece and said patient's eye as desired and attaching said guide template to said docking piece;

aligning said cutting piece with said docking piece, said guide template, and said patient's eye as desired;

placing said cutting piece within said docking piece in said assembled position, inserting said cutting blades into said patient's eye at desired LRI locations;

said step portion stopping said cutting piece and preventing further extension of said cutting blades into said patient's eye beyond desired LRI depths;

rotating said cutting piece relative to said docking piece about said rotational axis, forming arcuate LRIs in said patient's eye coaxial to said rotational axis said guide template raised stoppers stopping rotation of said cutting piece beyond desired LRI locations; and removing said cutting piece and said docking piece from said patient's eye.

12. The method according to claim 11, wherein:

said docking piece further comprises an opening to said suction chamber; and said suction chamber opening is configured for sealable attachment to a sub-atmospheric pressure source.

13. The method according to claim 12, wherein:

said docking piece further comprises a base handle;

said base handle comprises a housing;

said suction chamber opening connects to said base handle housing; and said base handle housing is configured for housing tubing connecting said suction chamber to said sub-atmospheric pressure source.

14. The method according to claim 11, further comprising the step of:

removing sub-atmospheric pressure from said docking piece suction chamber.

15. The method according to claim 11 wherein:

said cutting blades are positioned in 180-degree opposed relation; and said cutting blades are configured for making symmetrical incisions of equal length, depth, and curvature.

16. The method according to claim 11, further comprising the step of:

marking axes on said patient's eye; and wherein said aligning said docking piece proximal end on the sclera of said patient's eye comprises matching up said docking piece axis alignment markings with said marked axes on said patient's eye.

17. The method according to claim 11, wherein:

said rotating said cutting piece relative to said docking piece about said rotational axis comprises holding in a fixed position and rotating said cutting piece relative to said docking piece about said rotational axis.

\* \* \* \* \*